US012593766B2

(12) United States Patent
Bettis et al.

(10) Patent No.: US 12,593,766 B2
(45) Date of Patent: Apr. 7, 2026

(54) METHODS FOR GENERATING PLANTS PRODUCING SEEDS HAVING ALTERED SEED COMPOSITION

(71) Applicant: PIONEER HI-BRED INTERNATIONAL, INC., Johnston, IA (US)

(72) Inventors: Janel M Bettis, Urbandale, IA (US); John D Everard, Grimes, IA (US); Kristin Haug Collet, Des Moines, IA (US); Bo Shen, Johnston, IA (US); Shreedharan Sriram, Waukee, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 421 days.

(21) Appl. No.: 17/996,824

(22) PCT Filed: Apr. 22, 2021

(86) PCT No.: PCT/US2021/028550
§ 371 (c)(1),
(2) Date: Oct. 21, 2022

(87) PCT Pub. No.: WO2021/216811
PCT Pub. Date: Oct. 28, 2021

(65) Prior Publication Data
US 2023/0200322 A1 Jun. 29, 2023

Related U.S. Application Data

(60) Provisional application No. 63/014,320, filed on Apr. 23, 2020.

(51) Int. Cl.
*G16B 20/20* (2019.01)
*A01H 1/00* (2006.01)
*C12Q 1/6895* (2018.01)

(52) U.S. Cl.
CPC .......... *A01H 1/104* (2021.01); *C12Q 1/6895* (2013.01); *G16B 20/20* (2019.02); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 6,646,264 B1 * 11/2003 Modiano ............ G01N 21/3563
356/326
2013/0040826 A1 2/2013 Braun, III et al.
2018/0010142 A1 1/2018 Davies et al.
2019/0383733 A1 12/2019 Allen et al.

FOREIGN PATENT DOCUMENTS

CN 101204138 A 6/2008
WO WO 2018/160485 * 9/2018
WO 2020049491 A2 3/2020

OTHER PUBLICATIONS

Addo-Quaye C., et al., "Forward Genetics by Sequencing EMS Variation-Induced Inbred Lines", G3; Genes Genomes Genetics, vol. 7, No. 2, 2016, pp. 413-425. XP055698405, DOI: 10.1534/g3.116.029660.
Extended European Search Report for European Application No. EP21792504.9, mailed Aug. 12, 2024, 18 Pages.
Schierenbeck L., et al., "Fast Forward Genetics to Identify Mutations Causing a High Light Tolerant Phenotype in Chlamydomonas Reinhardtii by Whole-Genome-Sequencing," BMC Genomics, 2015, vol. 16 (57), pp. 1-15. XP021211218, doi: 10.1186/s12864-015-1232-y.
Tsuda, et al.: "Construction of a high-density mutant library in soybean and development of a mutant retrieval method using amplicon sequencing," BMC Genomics, Nov. 26, 2015 (Nov. 26, 2015), vol. 16.
International Search Report and Written Opinion for International Application No. PCT/US2021/028550, mailed Jul. 23, 2021.
International Preliminary Report on Patentability for International Application No. PCT/US2021/028550, mailed Nov. 3, 2022, 11 Pages.
Bolon Y-T., et al., "Phenotypic and Genomic Analyses of a Fast Neutron Mutant Population in Soybean," Plant Physiology, May 1, 2011, vol. 156, No. 1, pp. 240-253.
Partial Supplementary European Search Report for European Application No. EP21792504.9, mailed Apr. 22, 2024, 16 Pages.
Roesler K., et al., "An Improved Variant of Soybean Type 1 Diacylglycerol Acyltransferase Increases the Oil Content and Decreases the Soluble Carbohydrate Content of Soybeans[Open]," Plant Physiology, Jun. 2016, vol. 171, pp. 878-893.
Wang C.T., et al., "Mutagenesis: A Useful Tool for the Genetic Improvement of the Cultivated Peanut (*Arachis hypogaea* L.)," InTech, 2012, pp. 1-12.

* cited by examiner

*Primary Examiner* — Medina A Ibrahim

(57) ABSTRACT
Provided is a method for producing plants having seeds with an increased protein and/or oil content using mutagenesis and non-destructive chemical analysis. Additionally, provided are methods for identifying causative mutations associated with increased protein and/or oil content and methods of generating plants having the causative mutations associated with increased protein and/or oil content.

20 Claims, 7 Drawing Sheets

FIG. 5

METHODS FOR GENERATING PLANTS PRODUCING SEEDS HAVING ALTERED SEED COMPOSITION

CROSS REFERENCE TO RELATED APPLICATIONS

This application claims the benefit of priority to U.S. Provisional Patent Application No. 63/014,320, filed Apr. 23, 2020, the entire content of which is herein incorporated by reference.

FIELD OF THE INVENTION

The disclosure relates to the fields of molecular biology and biochemistry and, specifically, to methods for producing plants having an increased seed protein and/or oil content.

BACKGROUND

Plant seeds are a source of useful products, such as protein and oil, for human and animal consumption. Thus, generating plants with seeds having increased protein and oil content may contribute to a higher-value crop. However, in many seeds oil content shows a strong negative correlation with seed protein content, as increasing seed protein content usually leads to a reduction of seed oil content. Further, it is difficult to break the negative correlation and increase both protein and oil content in the seed.

Therefore, there is a need to develop methods to generate plants that produce seeds with increased protein and oil content. This disclosure provides such methods.

SUMMARY OF INVENTION

Provided herein are methods for producing plants having seeds with increased protein, comprising (a) providing a population of seeds having a genetic background and further comprising introduced mutations, (b) performing a high-throughput near infrared single-seed, non-destructive measurement of the protein or oil content of a plurality of seeds of the population of seeds, (c) setting a threshold protein or oil value based upon the measurement of protein or oil content respectively of the plurality of seeds, wherein the threshold protein or oil value is set above the average of the protein or oil content of the plurality of seeds, (d) separating seeds that exceed the threshold protein or oil value from the population of seeds, and (e) generating plants from the separated seeds that meet or exceed the threshold protein or oil value. In certain embodiments, prior to step (e) the method further comprises (i) performing a high-throughput near infrared single-seed, non-destructive measurement of either the protein content of the seeds from step (d) when the oil content is measured in step (b) or the oil content of the seeds from step (d) when the protein content is measured in step (b), (ii) setting a threshold protein value based upon the measurement of protein content of the seeds in step (i) or a threshold oil value based upon the measurement of oil content of the seeds in step (i), wherein the threshold protein or oil value is set above the average of the protein or oil content respectively of the seeds of step (i), and (iii) separating seeds that exceed the threshold values set in step (ii) from the seeds measured in step (i).

Further provided are methods for producing plants having seeds with increased oil and protein comprising (a) providing a population of seeds having a genetic background and further comprising one or more introduced mutations, (b)

performing a high-throughput near infrared single-seed, non-destructive measurement of the protein and oil content of a plurality of seeds of the population of seeds, (c) setting a threshold protein and oil value based upon the measurement of protein and oil content of the plurality of seeds, wherein the threshold value is set above the average of the protein and oil content of the plurality of seeds, (d) separating seeds that exceed the threshold oil and protein value from the population of seeds, and (e) generating plants from the separated seeds that exceed the threshold protein and oil value.

In certain embodiments of the methods described herein, the genetic background of the population of seeds is at least 90% homozygous. In certain embodiments of the methods described herein, the one or more introduced mutations comprise mutations that affect seed protein content, seed oil content, or seed yield.

In certain embodiments of the methods described herein, the population of seeds comprising one or more introduced mutations comprises at least 50,000 seeds. In certain embodiments of the methods described herein, the plurality of seeds of the population of seeds comprises at least 1000 seeds. In certain embodiments of the methods described herein, the population of seeds comprising one or more introduced mutations comprises between 10,000 to 10 million seeds and the plurality of seeds of comprises between 1000 to 50,000 seeds.

In certain embodiments of the methods described herein, the method further comprises repeating steps (b) to (e) with the remaining seeds of the population of seeds of (a). In certain embodiments, the method is repeated until the protein and/or oil content of each seed of the population of seeds is measured.

In certain embodiments of the methods described herein, the high-throughput single seed non-destructive measurement is performed using single seed near infrared spectroscopy (SS-NIR). In certain embodiments of the methods described herein, steps (b) to (d) occur sequentially in an NIR machine. In certain embodiments of the methods described herein, the high-throughput non-destructive determination is performed at a speed of at least 5 seeds per second.

In certain embodiments of the methods described herein, the accuracy of the single seed non-destructive protein or oil measurement is within 15% of the protein or oil amount measured using a standard reference analytical method of the seed. In certain embodiments of the methods described herein, the threshold protein value is a protein value that is at least 1.5 percentage points higher than the average protein value of the plurality of seeds. In certain embodiments of the methods described herein, the threshold oil value is an oil value that is at least 0.5 percentage points higher than the average oil value of the plurality of seeds. In certain embodiments of the methods described herein, the threshold protein value and/or the threshold oil value is set to separate at least 0.5% and less than 20% of the seeds from the population of seeds in step (c). In certain embodiments of the methods described herein, the threshold protein and oil value is a PROIL value that is at least 1.5 percentage points higher than the average PROIL value of the plurality of seeds.

In certain embodiments of the methods described herein, the method further comprises (f) collecting seeds from individual plants produced in (e), wherein the individual plants are optionally chosen based on one or more agronomic characteristics, (g) determining the average protein and/or oil content of the seeds collected from an individual plant of (f) using a second non-destructive chemical analysis, (h) identifying plants that produce seeds having an average protein and/or oil content that achieves a second threshold protein value and/or a second threshold oil value, (i) selecting the seeds from the plants of (h) that achieve the second threshold protein value and/or the second threshold oil value, and (j) generating plants from the seed collected in (i). In certain embodiments, the second non-destructive chemical analysis comprises a near infrared spectroscopy (NIRS) method such as near infrared reflectance (NIR), near infrared transmittance (NIT), single seed NIR (SS-NIR), bulk NIT, or Fourier transform NIR (FT-NIR). In certain embodiments, the second threshold protein value is a protein content of at least 34% by weight or a protein value that is at least 1.5 percentage points higher than the average value of the corresponding wild-type or control seed. In certain embodiments, the second threshold oil value is an oil content of at least 16% by weight or an oil value that is at least −2 percentage points higher than the average value of the corresponding wild-type or control seed. In certain embodiments, the separated seeds have a PROIL content of at least 52% by weight.

In certain embodiments of the methods described herein, the method further comprises (k) collecting seeds from individual plants generated in (j), wherein the individual plants are optionally chosen based on one or more agronomic characteristics; (l) determining the average protein and/or oil content of the seeds collected from an individual plant of (k) using a third non-destructive chemical analysis; (m) identifying plants that produce seeds having a seed protein and/or oil content that achieve a third threshold protein value and/or a third threshold oil value; (n) selecting the seeds from the individual plants of (m) that achieve the third threshold protein value and/or the third threshold oil value; and (o) generating plants from the seed selected in (n). In certain embodiments, the third non-destructive chemical analysis comprises a near infrared spectroscopy (NIRS) method such as near infrared reflectance (NIR), near infrared transmittance (NIT), single seed NIR (SS-NIR), bulk NIT, or Fourier transform NIR (FT-NIR). In certain embodiments, the third threshold protein value is a protein content of at least 34% by weight or a protein value that is at least 1.5 percentage points higher than the average value of the corresponding wild-type or control seed. In certain embodiments, the third threshold oil value is an oil content of at least 16% by weight or an oil value that is at least −2 percentage points higher than the average oil value of the corresponding wild-type or control seed. In certain embodiments, the separated seeds have a PROIL content of at least 52% by weight.

In certain embodiments, the method further comprises (p) collecting seeds from individual plants generated in (o), wherein the individual plants are optionally chosen based on one or more agronomic characteristics, (q) determining the average protein and/or oil content of the seeds collected from an individual plant of (p) using a fourth non-destructive chemical analysis, (r) identifying plants that produce seeds having a protein content and/or oil content that achieves a fourth average threshold protein value and/or a fourth average threshold oil value, (s) selecting the seeds from the individual plants of (r) that achieve a fourth average threshold protein value and/or a fourth average threshold oil value, and (t) generating plants from the seed selected in (r). In certain embodiments, the fourth non-destructive chemical analysis comprises a near infrared spectroscopy (NIRS) method such as near infrared reflectance (NIR), near infrared transmittance (NIT), single seed NIR (SS-NIR), bulk NIT, or Fourier transform NIR (FT-NIR). In certain embodiments, the fourth threshold protein value is a protein content of at least 34% by weight or a protein value that is at least 1.5 percentage points higher than the average value of the corresponding wild-type or control seed. In certain embodiments, the fourth threshold oil value is an oil content of at least 16% by weight or an oil value that is at least −2 percentage points higher than the average oil value of the corresponding wild-type or control seed. In certain embodiments, the separated seeds have a PROIL content of at least 52% by weight.

In certain embodiments of the methods described herein, the individual plants from which the seeds are collected in (f), (k), and/or (p) are chosen based on one or more agronomic or seed composition characteristic such as disease resistance, insect resistance, herbicide resistance, yield, early vigor, stand count, grain quality, amino acid content, sucrosyl-oligosaccharide content, plant height, nitrogen use efficiency, drought resistance, standability, abiotic stress resistance, and relative maturity.

In certain embodiments, the method further comprises determining the yield of the plants generated in (e), (j), (o), and/or (t) and selecting plants that have a yield higher than or within 3% as compared to the corresponding wild-type or control plant.

In certain embodiments, the method further comprises introducing mutations into the population of seed prior to step (a) by (i) treating a collection of seeds with a mutagen to produce a mutant population of seeds, (ii) growing plants comprising one or more introduced mutations from the mutant seed population, and (iii) collecting the population of seeds from the plants grown in step (ii). In certain embodiments the mutagen is a chemical mutagen such as base analogues, 5-bromo-uracil, 8-ethoxy caffeine, antibiotics, alkylating agents, sulfur mustards, nitrogen mustards, epoxides, ethylenamines, sulfates, sulfonates, sulfones, lactones, azide, hydroxylamine, nitrous acid, and acridines. In certain embodiments, the mutagen is radiation such as x-rays, gamma rays, neutrons, beta radiation, and ultraviolet radiation. In certain embodiments, the mutagen is a gamma ray administered at a dose of at least 50 Gray.

In certain embodiments of the methods described herein the plant is selected from the group consisting of cotton, soybean, safflower, sunflower, *Brassica*, maize, alfalfa, palm, and coconut.

Further provided is a method for identifying one or more causative mutations in a population of seed comprising (a) sequencing genomic DNA of an individual plant producing seeds having increased protein and/or oil content selected based on the methods described herein to create a consensus sequence, (b) mapping the consensus sequence from the individual plant of (a) to a reference genome sequence, (c) identifying genomic positions that are different between the reference genome sequence and the consensus sequence, thereby identifying variants in the plant, (d) comparing the sequence variants identified for the plant in (c) to sequence variants identified in at least one additional plant of the same generation and descending from (e.g., F1, F2, F3, F4, or F5 selfed progeny) the same seed as the plant of (c), and (e) identifying the set of mutations that occurred in both the plant in (c) and the at least one additional plant, thereby identifying causative mutations for a first mutant plant line. In certain embodiments, the sequence variants are selected from the group consisting of single nucleotide polymorphism (SNP), InDel, and/or a large deletion. In certain embodiments, the sequencing comprises a genome-wide sequence analysis. In certain embodiments, the method further comprises, (f) comparing the causative mutations identified for a first mutant line and the causative mutations identified for at least one additional mutant plant line, and (g) selecting the mutations that are unique to the first mutant line.

In certain embodiments of the method for identifying one or more causative mutations, after (c) and before (d) the method further comprises (i) mapping the position of the identified variants to the corresponding position of an annotated gene model of the reference genome sequence, and (ii) identifying the variants occurring within the boundaries of the annotated gene model. In certain embodiments, the method further comprises, (iii) determining if the variant identified within the boundaries of the annotated gene model causes a change in the amino acid sequence of the annotated gene, and (iv) selecting the variants that cause a change in the amino acid sequence.

Also provided is a method for plant breeding comprising (a) providing a population of seeds having a genetic background and further comprising one or more introduced mutations, the population comprising the progeny of M0 seeds treated with a mutagen; (b) performing a high-throughput near infrared single-seed, non-destructive measurement of the protein or oil content of a plurality of seeds of the population of seeds; (c) setting a threshold protein or oil value based upon the measurement of protein or oil content respectively of the plurality of seeds, wherein the threshold protein or oil value is set above the average of the protein or oil content of the plurality of seeds; (d) separating seeds that exceed the threshold protein or oil value from the population of seeds to produce a plurality of separated single seeds that exceed the threshold protein or oil value; (e) producing progeny seeds from individual plants grown from the separated single seeds of step (d); (f) growing plants from the progeny seeds produced in step (e) to create a mutant plant line comprising a plurality of plants descended from the same single seed of step (d); (g) sequencing genomic DNA from a plant, or seed therefrom, of a single plant of the mutant line produced in step (f) to create a consensus sequence; (h) mapping the consensus sequence to a reference genome sequence; (i) identifying one or more genomic positions that are different between the reference genome sequence and the consensus sequence, thereby identifying one or more sequence variants in the consensus sequence of step (h); (j) repeating steps (g) to (i) for at least another single plant of the mutant line produced in step (f); (k) identifying the variants of the first mutant plant line by comparing (i) the one or more sequence variants from the plant, or seed thereof, of step (i) to (ii) to the one or more sequence variants of the at least one additional plant of step (j) and selecting the variants that occurred in both (i) and (ii) as the variants of the first mutant plant line; (l) repeating steps (f) to (k) to identify variants of a second mutant plant line descended from a different single seed of step (d) as the first mutant plant line; and (m) identifying mutations causative for high oil or high protein in the first mutant plant line by comparing (i) the variants of the first mutant plant line to (ii) the variants of the second mutant plant line and selecting variants that occur in (i) and not in (ii) as causative mutations of the first mutant plant line. In certain embodiments, the method further comprises (n) mapping the position of the causative mutations or variants of the first mutant plant line to a corresponding position of an annotated gene model of the reference genome sequence, the annotated gene model comprising annotated genes; (o) identifying at least one of the identified causative mutations or variants occurring within the boundaries of one of the annotated genes; (p) determining if the mutation or variant within the boundaries of the annotated gene model causes a change in the amino acid sequence of the annotated gene; and (q) selecting the variants or causative mutations that cause a change in the amino acid sequence. In certain embodiments, the method further comprises introducing the one or more causative mutations of the first mutant plant line into a different plant, for example, by genome editing.

Also provided is a method for increasing seed protein and/or seed oil content in a plant, the method comprising introgressing one or more of the identified causative mutations into the plant.

Further provided is a method for increasing seed protein and/or seed oil content in a plant, the method comprising expressing in the plant a recombinant DNA construct comprising a gene comprising one or more of the identified causative mutations.

Also provided is a method for increasing seed protein and/or seed oil content in a plant comprising introducing a targeted genetic modification to insert one or more of the identified causative mutations into the plant. In certain embodiments, the targeted genetic modification is introduced using a genome modification technique selected from the group consisting of a polynucleotide guided endonuclease, CRISPR-Cas endonucleases, base editing deaminases, a zinc finger nuclease, a transcription activator-like effector nuclease (TALEN), engineered site-specific meganucleases, or Argonaute.

BRIEF DESCRIPTION OF THE DRAWINGS

The disclosure can be more fully understood from the following detailed description and the accompanying drawings, which form a part of this application.

FIG. 5 is a graph showing the top 50 high protein and oil mutants that were identified from 3800 M2 plants. Each dot is the average oil and protein content at 13% moisture of a single M2 plant by FT-NIR.

DETAILED DESCRIPTION

Figure 1:
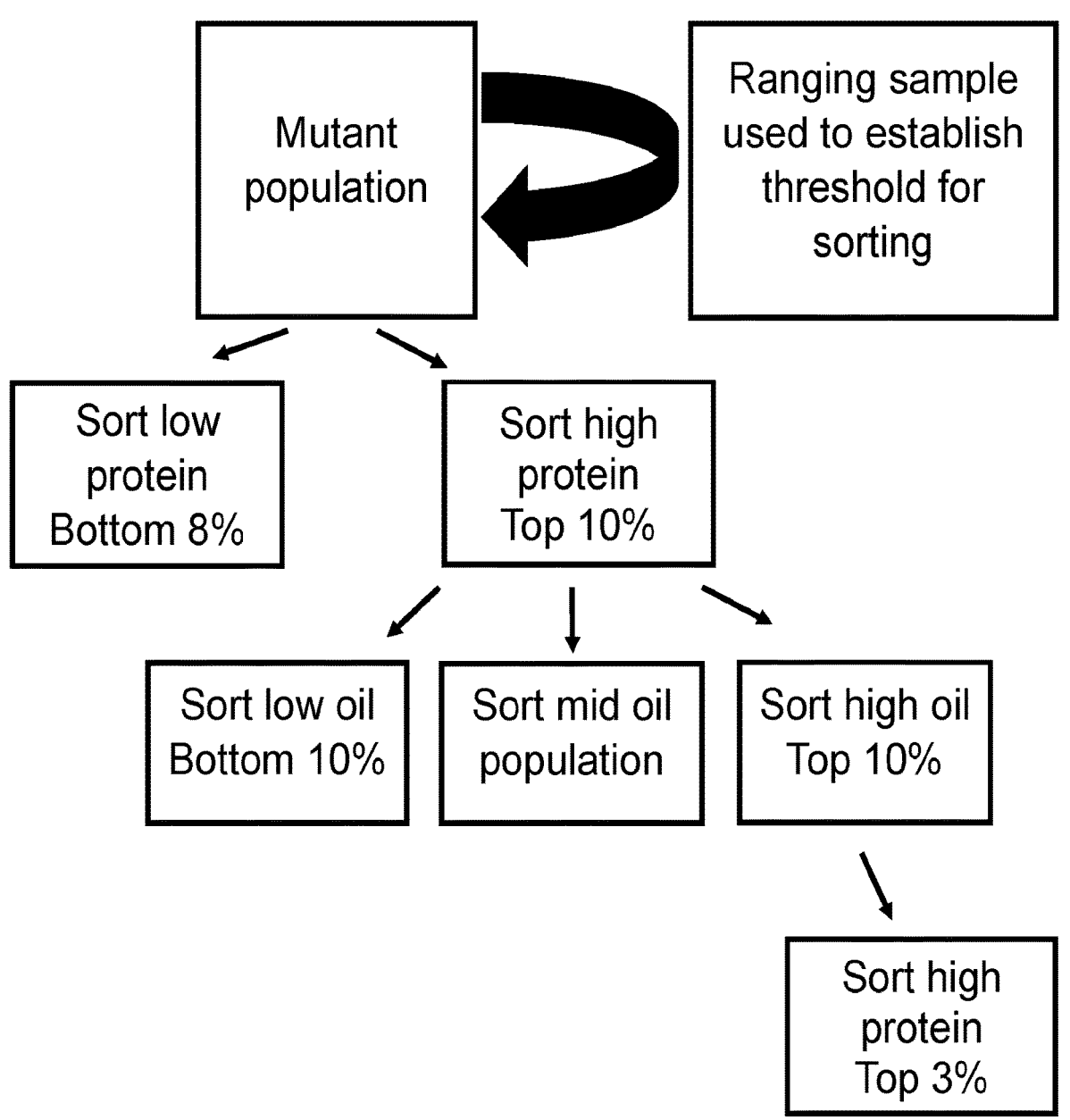
FIG. 1 is a schematic providing a generalized method to separate seed achieving a desired threshold level of protein and oil.

The present disclosure provides methods for generating plants that produce seeds with increased protein and/or oil content.

In certain embodiments, the method comprises (a) providing a population of seeds having a genetic background and further comprising introduced mutations, (b) performing a high-throughput near infrared single-seed, non-destructive measurement of the protein or oil content of a plurality of seeds of the population of seeds, (c) setting a threshold protein or oil value based upon the measurement of protein or oil content respectively of the plurality of seeds, wherein the threshold protein or oil value is set above the average of the protein or oil content of the plurality of seeds, (d) separating seeds that exceed the threshold protein or oil value from the population of seeds, and (e) generating plants from the separated seeds that exceed the threshold protein or oil value. In certain embodiments, prior to step (e), the method further comprises (i) performing a high-throughput near infrared single-seed, non-destructive measurement of either the protein content of the seeds from step (d) when the oil content is measured in step (b) or the oil content of the seeds from step (d) when the protein content is measured in step (b), (ii) setting a threshold protein value based upon the measurement of protein content of the seeds in step (i) or a threshold oil value based upon the measurement of oil content of the seeds in step (i), wherein the threshold protein or oil value is set above the average of the protein or oil content respectively of the of seeds of step (i), and (iii) separating seeds that exceed the threshold values set in step (ii) from the seeds measured in step (i).

In certain embodiments, the high-throughput, single-seed, non-destructive measurement can be repeated for the seeds separated that achieve the protein and/or oil content threshold. For example, in certain embodiments after the seeds that achieve the protein or oil threshold are separated and prior to generating the plant, the method may comprise performing a high-throughput near infrared single-seed, non-destructive measurement of the protein or oil content of the separated seeds that achieve the threshold protein and oil content, setting a threshold protein or oil value based upon the measurement of protein or oil content respectively of the plurality of seeds, wherein the threshold protein or oil value is set above the average of the protein or oil content of the separated of seeds, separating seeds that exceed the threshold protein or oil value from the population of seeds.

In certain embodiments, the method comprises (a) providing a population of seeds having a genetic background and further comprising one or more introduced mutations, (b) performing a high-throughput near infrared single-seed, non-destructive measurement of the protein and oil content of a plurality of seeds of the population of seeds, (c) setting a threshold protein and oil value based upon the measurement of protein and oil content of the plurality of seeds, wherein the threshold value is set above the average of the protein and oil content of the plurality of seeds, (d) separating seeds that exceed the threshold oil and protein value from the population of seeds, and (e) generating plants from the separated seeds that exceed the threshold protein and oil value.

In certain embodiments, the genetic background of the population of seeds having a genetic background and further comprising introduced mutations is at least 70%, 75%, 80%, 85%, 90%, 91%, 92%, 93%, 94%, 95%, 96%, 97%, 98%, 99%, or 100% homozygous. Percent identity is determined by comparing a statistically significant number of the homozygous alleles of the varieties. For example, a percent identity of 90% between two varieties means that the two varieties have the same alleles at 90% of their loci. In certain embodiments, the one or more introduced mutations comprise mutations affecting seed protein content, seed oil content, or seed yield.

In certain embodiments, the population of seeds having a genetic background and further comprising introduced mutations comprises at least 10,000, 50,000, 100,000, 200,000, 300,000, 400,000, 500,000, 600,000, 700,000, 800,000, 900,000, 1,000,000, 2,000,000, 3,000,000, 4,000,000, 5,000,000, 10,000,000 or 50,000,000 seeds and less than 100,000,000, 50,000,000 10,000,000, 7,500,000, 5,000,000, 2,500,000, 1,000,000, 900,000, 800,000, 700,000, 6,000,000, or 5,000,000 seeds. In certain embodiments, the plurality of seeds of the population of seeds comprises at least 500, 750, 1000, 2500, 5000, 10,000, 15,000, 20,000, 25,000, 30,000, 35,000, 40,000, 45,000, 50,000, 60,000, 70,000, 80,000, or 90,000 seeds and less than 250,000, 200,000, 150,000, 100,000, 75,000, 50,000, 25,000, or 10,000 seeds. In certain embodiments the population of seeds having a genetic background and further comprising introduced mutations comprises between 10,000 to 10 million seeds and the plurality of seeds of comprises between 1000 to 50,000 seeds.

In certain embodiments of the methods described herein, the method further comprises repeating the steps of performing a high-throughput near infrared single-seed, non-destructive measurement of the protein or oil content of a plurality of seeds of the population of seeds, setting a threshold protein or oil value based upon the measurement of protein or oil content respectively of the plurality of seeds, wherein the threshold protein or oil value is set above the average of the protein or oil content of the plurality of seeds, and separating seeds that exceed the threshold protein or oil value from the population of seeds at least once (e.g., 1, 2, 3, 4, 5, 6, 7, 8, 9, 10, 15, or 20 times). In certain embodiments, the steps are repeated until the protein and/or oil content of at least 80%, 85%, 90%, 91%, 92%, 93%, 94%, 95%, 96%, 97%, 98%, 99%, or 100% of the population of seeds having a genetic background and further comprising introduced mutations is measured. In certain embodiments, the plurality of seeds from each repeat is from the seeds remaining from the population of seeds. In certain embodiments, the plurality of seeds from each repeat is a combination of seeds remaining from the population of seeds and seeds from a previously tested plurality of seeds. In certain embodiments in which the steps are repeated at least once, the threshold protein and/or oil value is set specific to the plurality of seeds tested in the repeat.

As used herein a "non-destructive measurement" refers to a method whereby a component value (e.g., protein and/or oil content) of a seed is determined without significantly altering the viability (e.g., germination) of the seed. The non-destructive chemical analysis for use in the methods described herein may be any analysis method known in the art and may be selected based on the throughput, precision, and/or accuracy of the method.

Near Infrared Spectroscopy (NIRS) is a non-destructive tool for analyzing seed composition, with measurements based on the absorption of light energy (about 780 to 2500 nm) by $H_2O$, C—C, C—H, O—H, N—H, S—H and C=O bonds in the organic constituents of the materials being analyzed. The present disclosure provides methods which are based on NIRS and on the absorption of light energy, in the near-infrared spectrum range (780 to 2500 nm), in the organic constituents of the materials being analyzed. Near infrared reflectance (NIR) and near infrared transmittance (NIT) light spectra can be collected and used. For example, methods described herein can be carried out as single-seed NIR (SS-NIR), bulk NIT or FT-NIR. The absorption of the light energy is proportional to the concentration of the constituent of interest and the modified light comprising one or more of transmitted and reflected light spectra from the seed can be converted to accurately measure the amounts or concentrations of the constituent of interest, such as a protein and/or oil content. "Modified light" as used in the context of this disclosure means light that is transmitted (transmitted light) and/or reflected (reflected light) from a seed or other object such as soybean meal or defatted soybean flakes after receiving light from a light source. Transflected light is a combination of reflected and transmitted light and is included in modified light.

In some embodiments, spectrometers are used to collect spectra from samples of plants (e.g., soybeans), such as single seeds (e.g., SS-NIR), batches of seed from a single plant (e.g., FT-NIR), or bulk samples from a field plot (e.g., NIT). Measurements taken are compared to the standard reference analytical method for samples sizes (single seeds or bulk samples). In some embodiments a diverse array of seed (e.g., soybean) samples grown in different seasons and different environments that display a wide range in the concentrations of the components are used to generate calibrations that provide for reliable and accurate measurements of the components. In the methods provided, the conversion from modified light spectra from the seed (e.g., soybean) to the concentration of the constituent of interest is determined by a referencing to spectra from seeds where the constituent of interest has been measured using the standard reference analytical method for the component of interest as disclosed herein. Interpreting the near infrared spectral region (780-2500 nm) of seeds is complex for a number of reasons. Absorption in this region contains weaker overtones or harmonics of the fundamental frequencies and in combination bands, where absorption occurs in two or more overlapping fundamental bond energies. The energy absorption and resulting spectra are therefore composite vibrational signals of all of the resonating bonds within the organic components and water in the seed being analyzed. The spectral signal from any specific component is deciphered from the background and is influenced by the matrix that it is embedded in. For example, the molecular specific signal within an intact seed can be influenced by the environment such as geographic location, growing season, storage conditions and conditions during measurement, the genetic background, and the presence of similar molecules.

In some embodiments, single individual intact seeds are analyzed one seed at a time, such as with single-seed NIR techniques (SS-NIR) utilizing reflected light, transmitted light or a combination thereof.

Following analysis according the methods described herein, the seed can be used in research and plant breeding programs. For example, the seed can be grown to produce a plant which is crossed with itself or another different plant to produce progeny seed.

In some embodiments, small bulk quantities of seed, such as the amount of seed harvested from a single plant (about 50-300 seeds) which may be homozygous, are analyzed together. FT-NIR, which utilizes reflectance NIR, can be used as in methods described herein for samples harvested from individual plants. In some embodiments, bulk seed analysis (bulk NIT methods) are provided which typically require a mass of at least or at least about 100 g, 200 g, 250 g, 300 g, 350 g, or 400 g and less than or less than about 2000 g, 1000 g, 900 g, 800 g, 700 g or 500 g of sample. Such methods are useful, for example, in the analysis of seed grown in field test plots and yield trials or from a bulk harvest and the identification of modified seed from unmodified seed. Such methods may include a step of sampling the seed using a sampling system such as AOCS Official Method Ac 1-45.

When a number of seeds are assayed together, an average for the measured values across the population of seeds may be obtained either by pooling the data collected from individual seeds from that population or by using methods in which a pooled sample of the soybean seeds are measured simultaneously.

In certain embodiments, the non-destructive measurement of the methods described herein is performed using a near infrared spectroscopy (NIRS) method (e.g., NIR, NIT, FT-NIR). In certain embodiments, the NIRS method is selected from the group consisting of near infrared reflectance (NIR), near infrared transmittance (NIT), single seed near infrared reflectance (SS-NIR), bulk NIT, or Fourier transform near infrared reflectance (FT-NIR).

In certain embodiments, the single seed near-infrared non-destructive measurement is performed using single seed near infrared reflectance (SS-NIR). In certain embodiments, the SS-NIR is performed in high-throughput.

In certain embodiments of the methods described herein, the steps of performing a high-throughput near infrared single-seed, non-destructive measurement of the protein or oil content of a plurality of seeds of the population of seeds, setting a threshold protein or oil value based upon the measurement of protein or oil content respectively of the plurality of seeds, wherein the threshold protein or oil value is set above the average of the protein or oil content of the plurality of seeds, and separating seeds that exceed the threshold protein or oil value occur sequentially in an NIR machine (e.g., the seeds are not removed from the NIR machine following the high-throughput single-seed, non-destructive measurement).

As used herein "high-throughput" refers to the number of seeds analyzed per unit time. The speed of the high-throughput method is not particularly limited and may be chosen by a person of ordinary skill in the art based upon the precision of the sorter and size of the seed. In certain embodiments, the high-throughput method is run at a rate of at least 1 seed/second, 2 seeds/second, 5 seeds/second 6 seeds/second, 7 seeds/second seeds/second, 8 seeds/second, 9 seeds/second, 10 seeds/second, 11 seeds/second, 12 seeds/second, 13 seeds/second, 14 seeds/second, 15 seeds/second, 20 seeds/second, 30 seeds/second, 40 seeds/second, 50 seeds/second, 60 seeds/second, 70 seeds/second, 80 seeds/second, 90 seeds/second, 100 seeds/second and less than 500 seeds/second, 450 seeds/second, 400 seeds/second, 350 seeds/second, 300 seeds/second, 250 seeds/second, 200 seeds/second, 150 seeds/second, 100 seeds/second, 90 seeds/second, 80 seeds/second, 70 seeds/second, 60 seeds/second, 50 seeds/second, 40 seeds/second, 30 seeds/second.

In certain embodiments, the high-throughput near infrared single-seed, non-destructive measurement of the protein and/or oil content of the seeds is determined based upon a calibration model determined from a seed population having diverse compositional ranges.

As used herein, a "calibration model" refers to a model developed based on the relationship of NIR measurements and reference analytical chemistry measurements of data comprising protein and/or oil content analyzed both by NIR and a reference analytical method collected from samples having diverse compositional ranges.

The protein and oil content measured in the seed in the high-throughput near infrared single-seed, non-destructive methods are based upon the calibration model of a seed population having diverse compositional ranges. In certain embodiments, the seed population for calibration comprises field grown plants (e.g., soybean), such as from a diverse genetic background, comprising a compositional diversity, such as, for example, a compositional diversity created using transgenic techniques. In certain embodiments, the control seed population comprises seed of the same genetic background as the mutant seed population, but not having been subjected to the mutagen used to generate the mutant seed population. In certain embodiments, the control seed population comprises wild-type or corresponding seed of the same genetic background as the mutant seed and transgenic seed that otherwise comprises the same genetic background as the mutant seed. In certain embodiments, the wild-type or control seed comprises a composition diversity created by growing the plants producing the seed in different geographical locations and/or under different growth conditions. As used herein, "compositional diversity" refers to variations in the total oil and protein of the seeds in the population, so that the population has a range of seed oil and protein levels. In certain embodiments, the control seed population comprises seeds having a range of seed oil content between 10% by weight to 35% by weight. In certain embodiments, the control seed population comprises seeds having a range of seed protein content between 25% (e.g., 26%, 27%, 28%, 29%, 30%, 31%, 32%, 33%, 34%, 35%, 36%, 37%, 38%, 39%, 40%, 41%, or 42%) by weight to 55% (e.g., 54%, 53%, 52%, 51%, 50%, 49%, 48%, 47%, 46%, 45%, 44%, 43%, 43%, 41%, 40%, 39%) by weight.

Accuracy, with respect to the composition of seed sample under analysis refers to the measured concentration or measured amount of the component of interest being similar to or the same as that obtained when running the standard reference analytical method on the same sample. The accuracy obtained using the methods described herein is reproducible across multiple seeds or seed samples and facilitates high-throughput assessment on the composition of soybean seeds. For example, if a population of at least 10, 20, 50, 100, 250, 500, 1,000, 5,000, 10,000, 1,000,000, or 10,000,000 soybean seeds are measured using individual single-seed analysis, the amount of protein and/or oil may be accurately determined to within parameters described herein for at least 75%, 80%, 85%, 90%, 91%, 92%, 93%, 94%, 95%, 96%, 97%, 98%, 99%, 99.5% or 99.9% of the population of seeds.

In certain embodiments, the accuracy of the single seed non-destructive protein measurement is within 15% (e.g., within 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, 0.5%) of the protein amount measured using a standard reference analytical method of the seed.

In certain embodiments, the accuracy of the single seed non-destructive oil measurement is within 15% (e.g., within 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, 0.5%) of the oil amount measured using a standard reference analytical method of the seed.

As used herein, "reference chemistry" refers to the benchmark values obtained for the measurements of the compositions analyzed herein, using standard wet chemistry reference analytical methods. As used herein, the "standard wet chemistry reference analytical method" used for measuring protein and/or oil is a chromatographic (wet-chemistry) technique performed using an AOCS (American Oil Chemists' Society) Official Method. For single seeds, assays can be used that have been benchmarked against the standard wet chemistry reference analytical methods. One of skill in the art will understand that certain substitutions in the components and steps used in the Official Methods may be made without affecting the results of the analysis. In certain embodiments, the standard reference analytical method used for measuring the moisture content of whole beans is AOCS Official Method Ac 2-41, which measures the weight loss of a sample after a defined period in a forced draft oven heated to 130° C. In certain embodiments, the standard reference analytical method used for measuring the moisture content of soybean powders is AOCS Official Method Ba 2a-38, which measures the weight loss of a sample after a defined period in a forced draft oven heated to 130° C. In certain embodiments, the standard reference analytical method used for measuring oil is AOCS Official Method Ba 3-38 which gravimetrically measures the oil content of powdered seed material after extraction with petroleum ether. In certain embodiments, the standard reference analytical method used for measuring protein content is AOCS Ba 4e-93 which determines the protein content of ground soybean powders by combustion analysis. In certain embodiments, the standard reference analytical method used for measuring PROM is the addition of the oil and protein contents determined by the standard reference analytical methods defined above. In certain embodiments, the standard reference analytical method used for determining fatty acid profiles is AOCS Official Method Ce 1 e-91 on methyl esters derived from oil samples extracted from soybean powders.

As used herein "threshold" refers to the value (e.g., level, amount, or content) that needs to be achieved or exceeded before a seed is collected (sorted). For example, the threshold protein value refers to the minimum amount of protein present in the tested seed necessary for the seed to be collected. Similarly, the threshold oil value refers to the minimum amount of oil present in the tested seed necessary for the seed to be collected. The threshold value (e.g., protein and/or oil) is not particularly limited and may be chosen based on the protein and/or oil content desired in the generated plants. In certain embodiments, when the protein and/or oil content is determined for bulk seed (e.g., using FT-NIR or NIT) the average protein or average oil content of the bulk seed, usually collected from a single plant or grouping of like plants, is used to determine if the threshold protein and/or threshold oil value is achieved.

In certain embodiments, the threshold protein value refers to the total amount of protein in the seed as determined based upon the amount of total protein in percentage points by weight in the seed. Accordingly, in certain embodiments, the threshold protein value is a seed protein percent by weight at 13% moisture of at least 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5% or 48% and less than 52%, 51.5%, 50%, 49.5%, 49%, 48.5%, 48%, 47.5%, 47%, 46.5%, 46%, 45.5% or 45%. In certain embodiments, the threshold protein value is determined based upon the percentage point increase in total protein of the mutant seed as compared to the average protein value of the plurality of seeds and, in certain embodiments, can be done without normalizing the values for the moisture content of the seed. Accordingly, in certain embodiments, the threshold protein value is an increase in total protein of at least a 0.1%, 0.5%, 1%, 1.5%, 2%, 2.5%, 3%, 3.5%, 4%, 4.5%, 5%, 6%, 7%, 8% or 9% and less 10%, 9.5%, 9%, 8.5%, 8%, 7.5%, 7%, 6.5%, 6%, 5.5%, 5%, 4.5%, 4%, 3.5%, 3% (values are percentage points by weight) as compared to the average protein value of the plurality of seeds. In certain embodiments, the threshold protein value is determined based upon the percentage point increase in total protein of the mutant population as compared to a control (e.g., wild-type) seed and, in certain embodiments, can be done without normalizing the values for the moisture content of the seed. Accordingly, in certain embodiments, the threshold protein value is an increase in total protein of at least a 0.5%, 1%, 1.5%, 2%, 2.5%, 3%, 3.5%, 4%, 4.5%, or 5% and less 10%, 9.5%, 9%, 8.5%, 8%, 7.5%, 7%, 6.5%, 6%, 5.5%, 5%, 4.5%, 4%, 3.5%, 3% (values are percentage points by weight) as compared to a control sample. The control sample may be derived from the population and accordingly have a similar moisture content.

In certain embodiments, the moisture contents between a control sample or plurality of seeds and a reference sample (e.g., a mutant seed) are within 0.1%, 0.2%, 0.3%, 0.4%, 0.5%, 0.6%, 0.7%, 0.8%, 0.9%, 1%, 1.5%, 2%, 2.5% or 3% of each other.

In certain embodiments, the threshold oil value refers to the total amount of oil in the seed as determined based upon the amount of oil in percentage points by weight in the seed. In certain embodiments, the threshold oil value is a seed oil percent by weight at 13% moisture of at least 14%, 14.5%, 15%, 15.5%, 16%, 16.5%, 17%, 17.5%, 18%, 18.5%, 19%, 19.5%, 20%, 20.5%, 21%, 22.5%, 23%, 23.5%, 24%, 24.5%, 25%, 25.5%, 26%, 26.5%, or 27% and less than 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5% or 20%. In certain embodiments, the threshold oil value is determined based upon the percentage change in total oil of the mutant seed as compared to the average oil value of the plurality of seeds and, in certain embodiments, can be done without normalizing the values for the moisture content of the seed. Accordingly, in certain embodiments, the threshold oil value is an increase in total oil of at least 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, or 1% (values are percentage points by weight) as compared to the average oil value of the plurality of seeds. In certain embodiments, the threshold oil value is determined based upon the percentage change in total oil of the mutant population as compared to a control (e.g., wild-type) seed and, in certain embodiments, can be done without normalizing the values for the moisture content of the seed. Accordingly, in certain embodiments, the threshold oil value is at least −4%, −3.5%, −3%, −2.5%, −2%, −1.5%, −1%, −0.5%, 0%, 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, 1%, or 0.5% (values are percentage points by weight) as compared to a control seed.

In certain embodiments, a threshold fatty acid value is used. Threshold fatty acid value refers to the amount of one or more specific oil components, such as fatty acid content, as a percent of the total amount of oil. In certain embodiments, the one or more specific oil components is one or more of the unsaturated fatty acids (e.g., oleic acid, palmitic acid, stearic acid, linoleic acid, linolenic acid, arachidic acid, and erucic acid,). In certain embodiments, the threshold fatty acid value is an oleic acid value as a percent of the total fatty acids of at least 25%, 30%, 35%, 40%, 45%, 50%, 55%, 60%, 65%, 70%, 75%, 80%, 85%, 90%, or 95% and less than 96%, 95%, 90%, 85%, 80%, 75%, 70%, 65%, 60%, 55%, 50%, 45%, 40%, 35%, or 30%. In certain embodiments, the threshold fatty acid value is determined based upon the percentage change in oleic acid of the mutant seed as compared to the average oleic acid value of the plurality of seeds and, in certain embodiments, can be done without normalizing the values for the moisture content of the seed. Accordingly, in certain embodiments, the threshold fatty acid value is an increase in oleic acid of at least 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, or 1% (values are percentage points by weight) as compared to the average oleic acid value of the plurality of seeds. In certain embodiments, the threshold fatty acid value is determined based upon the percentage change in oleic of the mutant population as compared to a control (e.g., wild-type) seed and, in certain embodiments, can be done without normalizing the values for the moisture content of the seed. Accordingly, in certain embodiments, the threshold fatty acid value is an increase in oleic acid of at least 0.5%, 1%, 2%, 3%, 4%, 5%, 6%, 7%, 8%, 9%, 10%, 15%, 20% or 30% and less than 35%, 30%, 25%, 20%, 15%, 10%, 9%, 8%, 7%, 6%, 5%, 4%, 3%, 2.5%, 2%, 1.5%, or 1% (values are percentage points by weight) as compared to a control seed.

In certain embodiments, the threshold fatty acid value is a linolenic acid value as a percent of the total fatty acids of at least 0.1%, 0.5%, 1%, 2%, 3%, 4%, 5% and less than 8%, 7%, 6%, 5%, 4%, 3%, 2.5%, 2%, 1.5%, 1%, 0.5%, or 0.25%. In certain embodiments, the threshold fatty acid value is determined based upon the percentage change in linolenic acid of the mutant seed as compared to the average linolenic acid value of the plurality of seeds and, in certain embodiments, can be done without normalizing the values for the moisture content of the seed. Accordingly, in certain embodiments, the threshold fatty acid value is a change in linolenic acid of at −4%, −3.5%, −3%, −2.5%, −2%, −1.5%, −1%, −0.5%, 0%, 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, 1%, or 0.5% (values are percentage points by weight) as compared to the average linolenic acid value of the plurality of seeds. In certain embodiments, the threshold fatty acid value is determined based upon the percentage change in linolenic of the mutant population as compared to a control (e.g., wild-type) seed and, in certain embodiments, can be done without normalizing the values for the moisture content of the seed. Accordingly, in certain embodiments, the threshold fatty acid value is a change in linolenic acid of at least −20%, −15%, −10%, −5%, −4%, −3.5%, −3%, −2.5%, −2%, −1.5%, −1%, −0.5%, 0%, 0.5%, 1%, 1.5%, 2%, 2.5%, 3%, 3.5%, 4%, 4.5%, or 5% and less than 10%, 9%, 8%, 7%, 6%, 5%, 4.5%, 4%, 3.5%, 3%, 2.5%, 2%, 1.5%, 1%, 0.5%, or 0% (values are percentage points by weight) as compared to a control seed.

In certain embodiments, the threshold protein and oil values are set based on a desired PROIL content. As used herein "PROIL" refers to the sum of the protein and oil content of the seed. In certain embodiments, the PROIL content is at least 52%, 53%, 54%, 55%, 56%, 57%, 58%, 59%, 60%, 61%, 62% or 63% and less than 70%, 65%, 60%, 59%, 58%, 57%, 56%, or 55% of the total seed weight at 13% moisture. In certain embodiments, the threshold protein and oil value is determined based upon the percentage change in the PROIL content of the mutant seed as compared to the average PROIL value of the plurality of seeds and, in certain embodiments, can be done without normalizing the values for the moisture content of the seed. Accordingly, in certain embodiments, the threshold protein and oil value is an increase in PROIL content of at least 0.5%, 1%, 1.5%, 2%, 2.5%, 3%, 3.5%, 4%, 4.5%, 5%, 6%, 7%, 8%, 9%, or 10% and less than 15%, 14%, 13%, 12%, 11%, 10%, 9%, 8%, 7%, 6%, 5%, 4.5%, 4%, 3.5%, 3%, 2.5%, 2%, 1.5%, or 1% (values are percentage points by weight) as compared to the average PROIL of the plurality of seeds.

In certain embodiments, the threshold protein and/or oil values are set based on a desired percentage of seeds to separate. In certain embodiments, the threshold protein value is set to separate at least 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 12.5%, 13%, 13.5%, 14%, 14.5%, 15%, 16%, 17%, 18%, or 19%) and less than 20%, 19%, 18%, 17%, 16%, 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, or 2% of the seeds from the population. In certain embodiments, the threshold oil value is set to separate at least 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 12.5%, 13%, 13.5%, 14%, 14.5%, 15%, 16%, 17%, 18%, or 19%) and less than 20%, 19%, 18%, 17%, 16%, 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, or 2% of the seeds from the population.

The term "percentage point" (pp) difference, change, increase or decrease refers to the arithmetic difference of two percentages, e.g. [transgenic or genetically modified value (%)–control value (%)]=percentage points. For example, a modified seed may contain 20% by weight of a component and the corresponding unmodified control seed may contain 15% by weight of that component. The difference in the component between the control and transgenic seed would be expressed as 5 percentage points.

"Percent increase" or "percent decrease" refers to a change or difference expressed as a fraction of the control value, e.g. {[modified/transgenic/test value (%)–control value (%)]/control value (%)}×100%=percent change., or {[value obtained in a first location (%)–value obtained in second location (%)]/value in the second location (%)}×100=percent change.

The protein and oil measurements assayed in the disclosed methods may be taken at any moisture content. In the measurements made in the methods disclosed herein the moisture content may be variable and not normalized.

The moisture content affects the weight percentages of components of the seed, with drier seeds generally having a higher weight percent of the component, such as oil or protein. When comparing NIR-based measurements with standard reference analytical methods, measurements may be taken in each case at the same moisture content of soybean, or if measurements are taken at different moisture contents, the values obtained can be corrected to the same moisture content. Measurements can, for example, be taken at or standardized to a moisture content by weight of at least or at least about 0.01%, 0.1%, 0.5%, 1%, 2%, 3%, 4%, 5%, 6%, 7%, 8%, 9%, 10%, 11%, 12%, 13%, 14%, 15% or 20% and less than or less than about 35%, 30%, 25%, 20%, 19%, 18%, 17%, 16%, 15%, 14%, 13%, 12%, 11%, 10%, 9% or 8%. Unless indicated to the contrary, when a particular percentage of oil or protein value is described it is given at or about 13% by weight moisture content.

In certain embodiments, the method further comprises collecting seeds from the individual plants generated from the separated seed of the high-throughput near infrared single-seed, non-destructive measurement of protein and/or oil content that exceed the threshold oil and/or protein value from the population of seeds, determining the average protein and/or oil content of the seeds collected from an individual plant using a second non-destructive chemical analysis, identifying plants that produce seeds having an average protein and/or oil content that achieves a second threshold protein value and/or a second threshold oil value, selecting the seeds from the plants of that achieve the second threshold protein value and/or second threshold oil value, and generating plants from the selected seeds. Such measurements may be taken or normalized to 13% moisture.

The second threshold protein value may be any threshold protein value described herein. In certain embodiments, the second threshold protein value is a seed protein percent by weight at 13% moisture of at least 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5% or 48% and less than 52%, 51.5%, 50%, 49.5%, 49%, 48.5%, 48%, 47.5%, 47%, 46.5%, 46%, 45.5% or 45%. In certain embodiments, the second threshold protein value is an increase in total protein of at least a 0.5%, 1%, 1.5%, 2%, 2.5%, 3%, 3.5%, 4%, 4.5%, or 5% and less 10%, 9.5%, 9%, 8.5%, 8%, 7.5%, 7%, 6.5%, 6%, 5.5%, 5%, 4.5%, 4%, 3.5%, 3% (values are percentage points by weight at 13% moisture) as compared to a control sample, which has a similar genetic background but lacks the introduced mutations.

The second threshold oil value may be any threshold oil value described herein. In certain embodiments, the second threshold oil value is a seed oil percent by weight at 13% moisture of at least 14%, 14.5%, 15%, 15.5%, 16%, 16.5%, 17%, 17.5%, 18%, 18.5%, 19%, 19.5%, 20%, 20.5%, 21%, 22.5%, 23%, 23.5%, 24%, 24.5%, 25%, 25.5%, 26%, 26.5%, or 27% and less than 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5% or 20%. In certain embodiments, the second threshold oil value is at least –4%, –3.5%, –3%, –2.5%, –2%, –1.5%, –1%, –0.5%, 0%, 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, 1%, or 0.5% (values are percentage points by weight at 13% moisture) as compared to a control sample, which has a similar genetic background but lacks the introduced mutations.

In certain embodiments, the second protein threshold and second oil threshold values are set to separate seeds having a PROM that content is at least 52%, 53%, 54%, 55%, 56%, 57%, 58%, 59%, 60%, 61%, 62% or 63% and less than 70%, 65%, 60%, 59%, 58%, 57%, 56%, or 55% of the total seed weight at 13% moisture.

In certain embodiments, the plants are selected based on achieving the second threshold protein level. In certain embodiments, the plants are selected based on achieving the second threshold oil level. In certain embodiments, the plants are selected based on achieving both the second threshold protein level and the second threshold oil level. The second non-destructive chemical analysis may be any non-destructive chemical analysis described herein (e.g., near infrared reflectance (NIR), near infrared transmittance (NIT), single seed NIR (SS-NIR), bulk NIT, or Fourier transform NIR (FT-NIR)). In certain embodiments, the second non-destructive chemical analysis is FT-NIR.

In certain embodiments, the plants from which the seeds are collected following one or more separations according to the methods described herein are chosen based on one or more agronomic or seed composition characteristics. The one or more agronomic or seed composition characteristics are not particularly limited and are reflective of the commercial markets and interests of those involved in the development of the plant. In certain embodiments, the one or more agronomic or seed composition traits is one or more of disease resistance (e.g., resistance to anthracnose, brown stem rot, cercospora, charcoal rot, southern stem canker, downy mildew, frogeye leaf spot, phytophthora, and the like), insect resistance, herbicide resistance, yield, grain quality, amino acid content, sucrosyl-oligosaccharide content, plant height, nitrogen use efficiency, drought resistance, standability, abiotic stress resistance, and relative maturity. In certain embodiments, the one or more agronomic characteristics is early vigor, stand count, and/or maturity.

In certain embodiments, the method further comprises collecting seeds from the individual plants generated from the seed of plants that achieve the second threshold protein value and/or second threshold oil value, determining the average protein and/or oil content of the seeds collected from an individual plant using a third non-destructive chemical analysis, identifying plants that produce seeds having an average protein and/or oil content that achieves a third average threshold protein value and/or a third average threshold oil value, selecting the seeds from the plants that achieve the third average threshold protein value and/or the third average threshold oil value, and generating plants from the selected seeds.

The third threshold protein value may be any threshold protein value described herein. In certain embodiments, the third threshold protein value is a seed protein percent by weight at 13% moisture of at least 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5% or 48% and less than 52%, 51.5%, 50%, 49.5%, 49%, 48.5%, 48%, 47.5%, 47%, 46.5%, 46%, 45.5% or 45%. In certain embodiments, the third threshold protein value is an increase in total protein of at least a 0.5%, 1%, 1.5%, 2%, 2.5%, 3%, 3.5%, 4%, 4.5%, or 5% and less 10%, 9.5%, 9%, 8.5%, 8%, 7.5%, 7%, 6.5%, 6%, 5.5%, 5%, 4.5%, 4%, 3.5%, 3% (values are percentage points by weight at 13% moisture) as compared to a control sample.

The third threshold oil value may be any threshold oil value described herein. In certain embodiments, the third threshold oil value is a seed oil percent by weight at 13% moisture of at least 14%, 14.5%, 15%, 15.5%, 16%, 16.5%, 17%, 17.5%, 18%, 18.5%, 19%, 19.5%, 20%, 20.5%, 21%, 22.5%, 23%, 23.5%, 24%, 24.5%, 25%, 25.5%, 26%, 26.5%, or 27% and less than 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5% or 20%. In certain embodiments, the third threshold oil value is at least −4%, −3.5%, −3%, −2.5%, −2%, −1.5%, −1%, −0.5%, 0%, 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, 1%, or 0.5% (values are percentage points by weight at 13% moisture) as compared to a control seed.

In certain embodiments, the third protein threshold and third oil threshold values are set to separate seeds having a PROIL that content is at least 52%, 53%, 54%, 55%, 56%, 57%, 58%, 59%, 60%, 61%, 62% or 63% and less than 70%, 65%, 60%, 59%, 58%, 57%, 56%, or 55% of the total seed weight at 13% moisture.

The third non-destructive chemical analysis may be any non-destructive chemical analysis described herein (e.g., near infrared reflectance (NIR), near infrared transmittance (NIT), single seed NIR (SS-NIR), bulk NIT, or Fourier transform NIR (FT-NIR)). In certain embodiments, the third non-destructive chemical analysis is NIT.

In certain embodiments, the method further comprises collecting seeds from the individual plants generated from the seed of plants that achieved the third threshold protein value and/or third threshold oil value, determining the average protein and/or oil content of the seeds collected from an individual plant using a fourth non-destructive chemical analysis, identifying plants that produce seeds having an average protein and/or oil content that achieves a fourth average threshold protein value and/or a fourth average threshold oil value, selecting the seeds from the plants that achieve the fourth average threshold protein value and/or the fourth average threshold oil value, and generating plants from the selected seeds.

The fourth threshold protein value may be any threshold protein value described herein. In certain embodiments, the fourth threshold protein value is a seed protein percent by weight at 13% moisture of at least 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5% or 48% and less than 52%, 51.5%, 50%, 49.5%, 49%, 48.5%, 48%, 47.5%, 47%, 46.5%, 46%, 45.5% or 45%. In certain embodiments, the fourth threshold protein value is an increase in total protein of at least a 0.5%, 1%, 1.5%, 2%, 2.5%, 3%, 3.5%, 4%, 4.5%, or 5% and less 10%, 9.5%, 9%, 8.5%, 8%, 7.5%, 7%, 6.5%, 6%, 5.5%, 5%, 4.5%, 4%, 3.5%, 3% (values are percentage points by weight at 13% moisture) as compared to a control sample.

The fourth threshold oil value may be any threshold oil value described herein. In certain embodiments, the fourth threshold oil value is a seed oil percent by weight at 13% moisture of at least 14%, 14.5%, 15%, 15.5%, 16%, 16.5%, 17%, 17.5%, 18%, 18.5%, 19%, 19.5%, 20%, 20.5%, 21%, 22.5%, 23%, 23.5%, 24%, 24.5%, 25%, 25.5%, 26%, 26.5%, or 27% and less than 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5% or 20%. In certain embodiments, the fourth threshold oil value is at least −4%, −3.5%, −3%, −2.5%, −2%, −1.5%, −1%, −0.5%, 0%, 0.5%, 1%, 1.5%, 2%, 2.5%, 3%, 3.5%, 4%, 4.5%, or 5% and less than 15%, 14%, 13%, 12%, 11%, 10%, 9%, 8%, 7%, 6%, 5%, 4.5%, 4%, 3.5%, 3%, 2.5%, 2%, 1.5%, 1%, or 0.5% (values are percentage points by weight at 13% moisture) as compared to a control seed.

In certain embodiments, the fourth protein threshold and fourth oil threshold values are set to separate seeds having a PROIL that content is at least 52%, 53%, 54%, 55%, 56%, 57%, 58%, 59%, 60%, 61%, 62% or 63% and less than 70%, 65%, 60%, 59%, 58%, 57%, 56%, or 55% of the total seed weight at 13% moisture.

The fourth non-destructive chemical analysis may be any non-destructive chemical analysis described herein (e.g., near infrared reflectance (NIR), near infrared transmittance (NIT), single seed NIR (SS-NIR), bulk NIT, or Fourier transform NIR (FT-NIR)). In certain embodiments, the fourth non-destructive chemical analysis is NIT.

The steps of collecting seeds from the individual plants generated from the seed of plants that achieved the threshold protein value and/or threshold oil value, determining the average protein and/or oil content of the seeds collected from an individual plant using a non-destructive chemical analysis, identifying plants that produce seeds having an average protein and/or oil content that achieves an average threshold protein value and/or an average threshold oil value, selecting the seeds from the plants that achieve the average threshold protein value and/or the average threshold oil value, and generating plants from the selected seeds may be further repeated such that in certain embodiments, the method may comprise a fifth, sixth, seventh, eighth, ninth, tenth, or so on threshold protein and/or oil value. The threshold protein and/or oil values may be any threshold values described herein and the non-destructive chemical analysis may be any non-destructive chemical analysis described herein.

The threshold protein value(s) (e.g., threshold protein value, second threshold protein value, third threshold protein value, and fourth threshold protein value) and threshold oil value(s) (e.g., threshold oil value, second threshold oil value, third threshold oil value, and fourth threshold oil value) described herein are each independently determined (selected), such that in certain embodiments the threshold values are the same. Alternatively, in certain embodiments at least one (e.g., at least 2, 3, or 4) threshold protein value and/or threshold oil value is different.

In certain embodiments, the plants generated from seeds separated in the high-throughput near infrared single-seed, non-destructive measurement of the protein or oil content and/or the seeds selected based on achieving the second, third, and/or fourth threshold protein value and/or oil value are further selected based on yield. In certain embodiments, the plants are selected based on having a yield that is greater than or within 0.5%, 1%, 1.5%, 2%, 2.5%, 3%, 3.5%, 4%, 4.5%, or 5%, as compared to the corresponding control plant, for example, one which has a similar genetic background but lacks the introduced mutations.

As used herein, "yield" refers to the amount of agricultural production harvested per unit of land and may include reference to bushels per acre or kilograms per hectare of a crop at harvest, as adjusted for grain moisture. Grain moisture is measured in the grain at harvest. The adjusted test weight of grain is determined to be the weight in pounds per bushel or kilogram, adjusted for grain moisture level at harvest.

In certain embodiments of the methods described herein, the population of seeds comprising one or more introduced mutations (i.e., the population of (a)) is produced by (i) treating a collection of seed with a mutagen to produce a mutant population of seed, (ii) growing plants comprising one or more introduced mutations from the mutant seed population, and (iii) collecting the population of seed from the plants grown in step (ii).

As used herein, a "mutagen" refers to any agent that causes a genetic mutation in the genetic material of the treated seed and plant grown therefrom. In certain embodiments, the mutagen is radiation or a chemical mutagen.

In certain embodiments, the mutagen is a chemical mutagen. The type of chemical mutagen is not particularly limited and can be selected by a person of ordinary skill in the art based upon the number and types of mutations desired. In certain embodiments, the chemical mutagen is one or more of base analogues, 5-bromo-uracil, 8-ethoxy caffeine, antibiotics, alkylating agents, sulfur mustards, nitrogen mustards, epoxides, ethylenamines, sulfates, sulfonates, sulfones, lactones, azide, hydroxylamine, nitrous acid, and acridines.

In certain embodiments, the mutagen is radiation. The type of radiation is not particularly limited and can be selected by a person of ordinary skill in the art based upon the number and types of mutations desired. In certain embodiments, the radiation is one or more of x-rays, gamma rays, neutrons, beta radiation, and ultraviolet radiation. In certain embodiments, the mutagen is a gamma ray. In certain embodiments, the gamma ray is administered to the seed at dose of at least 50 gray (Gy), 60 Gy, 70 Gy, 80 Gy, 90 Gy, 100 Gy, 120 Gy, 140 Gy, 160 Gy, 180 Gy, 200 Gy, 225 Gy, 250 Gy, 275 Gy, 300 Gy, 325 Gy, 350 Gy, 375 Gy, 400 Gy, 450 Gy, 500 Gy, 550 Gy, 600 Gy, 650 Gy, or 700 Gy) and less than 1500 Gy, 1400 Gy, 1300 Gy, 1200 Gy, 1100 Gy, 1000 Gy, 950 Gy, 900 Gy, 850 Gy, 800 Gy, 750 Gy, 700 Gy, 650 Gy, 600 Gy, 550 Gy, 500 Gy, 450 Gy, 400 Gy, 350 Gy, 300 Gy, 250 Gy, or 200 Gy. The gray (Gy) is a derived unit of ionizing radiation dose in the International System of Units (SI) as the absorption of one joule of radiation energy per kilogram of matter.

The plant of the methods described herein is not particularly limited and may be any plant for which increased protein or oil content in the seed is desired. Examples of plant species of interest include, but are not limited to, maize (*Zea mays*), *Brassica* sp. (e.g., *B. napus, B. rapa, B. juncea*), particularly those *Brassica* species useful as sources of seed oil, alfalfa (*Medicago sativa*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Hehanthus annuus*), safflower (*Carthamus tinctorius*), wheat (*Triticum aestivum*), soybean (*Glycine max*), tobacco (*Nicotiana tabacum*), peanuts (*Arachis hypogaea*), cotton (*Gossypium barbadense, Gossypium hirsutum*), coconut (*Cocos nucifera*), olive (*Olea europaea*), cashew (*Anacardium occidentale*), macadamia (*Macadamia integrifoha*), almond (*Prunus amygdalus*), green beans (*Phaseolus vulgaris*), and lima beans (*Phaseolus limensis*), peas (*Lathyrus* spp).

In certain embodiments, plants of the present disclosure are oil-seed plants (e.g., cotton, soybean, safflower, sunflower, *Brassica*, maize, alfalfa, palm, coconut, etc.) and/or leguminous plants (e.g., beans and peas; beans include guar, locust bean, fenugreek, soybean, garden beans, cowpea, mungbean, lima bean, fava bean, lentils, chickpea) In certain embodiments, soybean, sunflower, and/or *Brassica* plants are optimal, and in yet other embodiments soybean plants are optimal.

In certain embodiments the method further comprises identifying one or more causative mutations associated with the increased protein and/or oil content of the seed of the plants generated from seeds separated in the high-throughput near infrared single-seed, non-destructive measurement of the protein or oil content and/or the seeds selected based on achieving the second, third, and/or fourth threshold protein value and/or oil value. In certain embodiments, the method comprises (a) sequencing an individual plant, or seeds thereof, generated from seeds separated in the high-throughput near infrared single-seed, non-destructive measurement of the protein or oil content and/or the seeds selected based on achieving the second, third, and/or fourth threshold protein value and/or oil value to generate a consensus sequence; (b) mapping the consensus sequence of the individual soybean plant of (a) to a reference genome sequence; (c) identifying genomic positions that are different between the reference genome sequence and the consensus sequence, thereby identifying variants in the plant; (d) comparing the sequence variants identified for the plant in (c) to sequence variants identified in at least one additional plant of the same generation and descending from the same seed as the plant of (a); and (e) identifying the set of mutations that occurred in both the plant in (c) and the at least one additional plant, thereby identifying causative mutations for a first mutant line. In certain embodiments, the sequence variants are selected from the group consisting of a single-nucleotide polymorphism, and InDel, and/or a large deletion. In certain embodiments, the sequencing comprises genome wide sequence analysis.

"Reference genome sequence" as used herein refers to a digital nucleic acid sequence or set of nucleic acid sequences assembled from one or more individuals genomes and is a representative example of the set of genes of a species or variety.

In certain embodiments, genomic positions identified as containing a SNP, InDel, or large deletions contain at least 2, 3, 4, 5, 6, 7, 8, 9, or 10 or more reads, optionally with at least 50%, 55%, 60%, 65%, 70%, 75%, 80%, 85%, 90%, 95%, or 99% of the mapped bases at the position supporting the SNP or InDel, mapped at the identified SNP or InDel must be present.

As used herein, "InDel" refers to short insertions or deletions of nucleic acids. The number of base pairs of an InDel is not particularly limited and will usually comprise about 50 or less base pairs.

In certain embodiments, the method further comprises comparing the causative mutations identified for a first mutant line and the causative mutations identified for at least 1, 2, 3, 4, 5, 6, 7, 8, 9, 10, 20, 40, 60, or 100 additional mutant lines; and (g) selecting the mutations that are unique to the first mutant line.

In certain embodiments of the method the method further comprises (i) mapping the position of the identified variants or causative mutations to the corresponding position of an annotated gene model of the reference genome sequence, the annotated gene model comprising annotated genes; and (ii) identifying the mutations or variants occurring within the boundaries of one of the annotated genes of the annotated gene model. In certain embodiments the method further comprises (iii) determining if the variant or mutation identified within the boundaries of the annotated gene causes a change in the amino acid sequence of the annotated gene; and (iv) selecting the variants or mutations that cause a change in the amino acid sequence (e.g., non-synonymous mutation).

As used herein, a mutant plant line refers to plants that are filial generations (e.g., descendants) of a single seed. In certain embodiments the mutant plant line refers to the filial generations, optionally produced by selfing, of a single seed exceeding the threshold protein and/or oil value from the high-throughput near infrared single-seed, non-destructive measurement of the population of seeds comprising one or more introduced mutations. In certain embodiments, the plants of a mutant line are at least 95%, 96%, 97%, 98%, or 99% homozygous.

Further provided is a method for plant breeding comprising (a) providing a population of seeds having a genetic background and further comprising introduced mutations, the population comprising the progeny (e.g. M1 seeds) of M0 seeds treated with a mutagen; (b) performing a high-throughput near infrared single-seed, non-destructive measurement of the protein or oil content of a plurality of seeds of the population of seeds; (c) setting a threshold protein or oil value based upon the measurement of protein or oil content respectively of the plurality of seeds, wherein the threshold protein or oil value is set above the average of the protein or oil content of the plurality of seeds; (d) separating seeds that exceed the threshold protein or oil value from the population of seeds to produce a plurality of separated single seeds that exceed the threshold protein or oil value; (e) producing progeny seeds from the separated single seeds of step (d); (f) growing plants from the progeny seeds of one of the individual plants produced in step (e) to create a mutant plant line comprising a plurality of plants descended from the same single seed of step (d), each of the plurality of plants may be referred to herein as a subline of the mutant plant line; (g) sequencing genomic DNA from a plant, or seed therefrom, of a single plant (i.e., subline) of the mutant line produced in step (f) to create a consensus sequence; (h) mapping the consensus sequence to a reference genome sequence; (i) identifying one or more genomic positions that are different between the reference genome sequence and the consensus sequence, thereby identifying one or more sequence variants in the consensus sequence of step (h); (j) repeating steps (g) to (i) for another single plant of the mutant line produced in step (f); (k) identifying the variants of the first mutant plant line by comparing (i) the one or more sequence variants from the plant, or seed thereof, of step (i) to (ii) to the one or more sequence variants of the at least one additional plant of step (j) and selecting the variants that occurred in both (i) and (ii) as the variants of the first mutant plant line; (l) repeating steps (f) to (k) to identify variants of a second mutant plant line descended from a different single seed of step (d) as the first mutant plant line; and (m) identifying mutations causative for high oil or high protein in the first mutant plant line by comparing (i) the variants of the first mutant plant line to (ii) the variants of the second mutant plant line and selecting variants that occur in (i) and not in (ii) as causative mutations of the first mutant plant line.

The population of seeds having a genetic background and further comprising one or more introduced mutations may be any population of seeds described herein. In certain embodiments the population of seeds is produced by (i) treating a collection of seed with a mutagen to produce a mutant population of seed, (ii) growing plants comprising one or more introduced mutations from the mutant seed population, and (iii) collecting the population of seed from the plants grown in step (ii).

The high-throughput near infrared single-seed, non-destructive measurement may be any high-throughput near infrared single-seed, non-destructive measurement described herein. Similarly, the threshold protein or oil value may be any threshold protein or oil value described herein.

In certain embodiments, the method for plant breeding further comprises (n) mapping the position of the variants or causative mutations of the first mutant plant line to a corresponding position of an annotated gene model of the reference genome sequence, the annotated gene model comprising annotated genes; (o) identifying at least one of the identified variants or causative mutations occurring within the boundaries of one of the annotated genes; (p) determining if the mutation within the boundaries of the annotated gene model causes a change in the amino acid sequence of the annotated gene; and (q) selecting the variant or causative mutation that causes a change in the amino acid sequence. In certain embodiments, the method further comprises introducing the one or more causative mutations of the first mutant plant line into a different plant, for example, by genome editing.

In certain embodiments, the single seed of the population of seeds comprising one or more introduced mutations is referred to as the M0 generation. In certain embodiments, M1 is used to identify the first generation, e.g., selfed progeny, of the M0 generation. Similarly, M2, M3, M4 and so on is used to identify further generations of the M0, for example, M2 is used to identify the second generation, e.g., selfed progeny of the M1 generation, of the M0 generation. The methods can be used with any of the generations disclosed herein.

As used herein, "mapping" refers to the process of aligning short sequence reads to a reference sequence.

As used herein, "consensus sequence" "consensus base sequence" or the like refers to the calculated order of the most frequent residues found at each position of a sequence alignment. In certain embodiments, the consensus base sequence is the most frequent residues found at each position of the sequences generated for the seeds of an individual plant.

The term "causative mutation" or the like refers to a mutation at a particular locus that confers, or contributes to, a desirable phenotype, e.g., increased protein and/or oil content of the seed. In certain embodiments, the causative mutation identified results in change in the amino acid sequence of a gene of the plant. In certain embodiments, the causative mutation is found in a non-translated region, such as, for example, an intronic region or regulatory region.

In certain embodiments, the identified variants and/or causative mutations are markers genetically linked to quantitative trait loci (QTLs) associated with the increased protein and/or oil content of the mutant seeds. In certain embodiments, the markers are used for identifying and producing plants comprising the QTL associated with increased protein and/or oil content.

As used herein, "genetically linked" refers to genetic loci that are in linkage disequilibrium and statistically determined not to assort independently.

In certain embodiments of the methods described herein, the method consists essentially of the recited steps. As used herein, the term "consisting essentially of" is intended to cover a non-inclusive inclusion so long as the inclusion does not alter the principle operation of the recited method.

In certain embodiments, the method further comprises isolating the gene(s) comprising a causative mutation (e.g., non-synonymous mutation(s)) and expressing the gene(s) comprising the mutation, optionally individually, in plants to determine the effect on seed protein and/or oil content.

In certain embodiments, the method further comprises introducing into a plant cell a gene comprising a causative mutation (e.g., mutated gene) associated with increased seed protein and/or oil content identified herein and generating a plant from the plant cell, wherein the plant comprises the gene associated with increased seed protein and/or oil content.

In certain embodiments, the gene is introduced by transformation. Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563, 055 and 5,981,840), direct gene transfer (Paszkowski et al. (1984) *EMBO J.* 3:2717-2722), and ballistic particle acceleration (see, for example, U.S. Pat. Nos. 4,945,050; 5,879, 918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann.*

*Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) Annals of Botany 75:407-413 (rice); Osjoda et al. (1996) *Nature Biotechnology* 14:745-750 (maize via *Agrobacterium tumefaciens*); all of which are herein incorporated by reference.

In certain embodiments, the method further comprises introducing into a regenerable plant cell a targeted genetic modification that introduces a causative mutation identified herein into a gene associated with increased seed protein and/or oil content and generating the plant wherein the plant comprises the targeted genetic modification and produces seeds having increased protein and/or oil content.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion.

Methods to modify or alter endogenous genomic DNA are known in the art. For example, a pre-existing or endogenous sequence in a host plant can be modified or altered in a site-specific fashion using one or more site-specific engineering systems. Modification of polynucleotides may be accomplished, for example, by introducing single- or double-strand breaks into the DNA molecule.

Double-strand breaks induced by double-strand-break-inducing agents, such as endonucleases that cleave the phosphodiester bond within a polynucleotide chain, can result in the induction of DNA repair mechanisms, including the non-homologous end-joining pathway, and homologous recombination. Endonucleases include a range of different enzymes, including restriction endonucleases (see e.g. Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, DC)), meganucleases (see e.g., WO 2009/114321; Gao et al. (2010) Plant Journal 1:176-187), TAL effector nucleases or TALENs (see e.g., US20110145940, Christian, M., T. Cermak, et al. 2010. Targeting DNA double-strand breaks with TAL effector nucleases. Genetics 186(2): 757-61 and Boch et al., (2009), Science 326(5959): 1509-12), zinc finger nucleases (see e.g. Kim, Y. G., J. Cha, et al. (1996). "Hybrid restriction enzymes: zinc finger fusions to FokI cleavage"), and CRISPR-Cas endonucleases (see e.g. WO2007/025097 application published Mar. 1, 2007).

Also provided herein, are plants generated from any of the methods described herein (e.g., plants selected based on one or more non-destructive chemical analyses, plants introgressed with a causative mutation(s) associated with increased protein and/or oil content, plants transformed with a causative mutation(s) associated with increased protein and/or oil content, plants transformed with a gene(s) identified to be associated with increased protein and/or oil content, and plants comprising a targeted genetic modification that introduces a mutation in a gene(s) identified to be associated with increased protein and/or oil content).

Further provide herein are methods for producing plants having seeds with increased beneficial seed component characteristics. In said methods the non-destructive measurements of the methods described herein are calibrated to determine the seed content of the desired seed component and the threshold values are based on the desired level of the beneficial seed component.

As used herein, "beneficial seed component" may be a component in which increased content in the seed may be beneficial (e.g., protein) or alternatively a component in which a decreased content in the seed may be beneficial (e.g., stachyose). A person of ordinary skill in the art can readily identify components that increased content or decreased content is desirable in the resulting seed, such as, for example, producing seeds with a high essential amino acid content, increased unsaturated fatty acids, increased isoflavones, and/or decreased sucrose oligosaccharides, such as stachyose.

In certain embodiments, the at least one beneficial seed characteristic is protein, oil, amino acids, essential amino acids, carbohydrates, minerals, sucrosyl-oligosaccharide, unsaturated fatty acids, monounsaturated fatty acids, polyunsaturated fatty acids, isoflavones (e.g., genistein), and sugars.

The following are examples of specific embodiments of some aspects of the invention. The examples are offered for illustrative purposes only and are not intended to limit the scope of the invention in any way. Efforts have been made to ensure accuracy with respect to numbers used (e.g., amounts, temperatures, etc.), but some experimental error and deviation should, of course, be allowed for.

Example 1

This example demonstrates the generation of a population of seeds from plants comprising one or more introduced mutations using gamma-ray, fast neutron, or EMS.

To generate the gamma-ray mutant population a proprietary maturity group III soybean variety was used. Briefly, approximately 10,000 seeds were irradiated at a dose of either 100 Gy, 200 Gy, or 300 Gy using $^{60}$Co gamma radiation at the Pennsylvania State University Radiation Science and Engineering Center (RSEC). Treated seed were planted in a field to generate M2 seeds. The M2 seeds on the M1 plants were harvested by a combine in bulk and used for single seed protein and oil sorting on a high throughput seed sorter, described below, to assess the composition of each seed.

To generate the fast neutron mutant population a proprietary maturity group III soybean variety was used. Briefly, approximately 120,000 seeds were exposed to a fast neutron radiation dose of 20 Gy at the McClellan Nuclear Radiation Center at the University of California-Davis. Treated seeds were planted in field to generate M2 seeds. M2 seeds on M1 plants were harvested by a combine in bulk and used for single seed protein and oil sorting on a high throughput seed sorter, described below, to assess the composition of each seed.

To generate the EMS mutant population a proprietary maturity group III soybean variety was used. Briefly, approximately 10,000 seeds were soaked in 25 MINI (0.3%), 8.3 mM (0.1%), or 0.83 mM (0.01%) ethyl methanesulfonate (EMS) solution for 6 hours followed by 3 washes with water. EMS was then neutralized by 10% sodium thiosulfate solution. Treated seeds were air dried and planted in field. A single M2 seed was collected from individual M1 plant for developing individual M2 lines. The remaining seeds from the M1 plants were harvested in bulk for single seed sorting for high protein and oil mutant screening.

Example 2

This example demonstrates the generation of calibration models for protein content and oil content and the development of a protein and oil threshold value.

High speed single seed sorting was performed on a Q-Sorter Explorer optimized for the singulation and transport of soybean seed. In order to calibrate the instruments, near infrared spectra (900-1700 nm) were captured for a population of soybeans that had been selected because of their very wide compositional range (Table 1).

TABLE 1

Oil, protein, oleic and linolenic acid compositions of soybeans used to calibrate the Q-Sorter. Values were obtained using the reference chemistry methods described in WO 2018/160485 A1.

| Constituent | Average | SD | Min | Max |
|---|---|---|---|---|
| Oil (wt %; as is) | 21.1 | 2.2 | 12.8 | 29.7 |
| Protein (wt % DB) | 39.4 | 3.7 | 30.9 | 50.4 |
| Oleic Acid (rel %) | 64.8 | 24.1 | 12.2 | 85.4 |
| Linolenic Acid (rel %) | 3.8 | 2.0 | 1.7 | 13.3 |

The population of field grown soybeans was unique, and the compositional diversity had been created in elite germplasm using transgenic techniques such as those listed in US Patent Publication No. 2019-0383733. The seed used to create the calibrations was selected from across the compositional range. Spectra for each individual bean was collected by passing it through the sorter three times. The individual beans were then subjected to reference chemistry using methods described in US Patent Publication No. 2019-0383733. Spectral data and reference chemistry were then combined using chemometric techniques to create predictive algorithms (calibration models) that were used to sort the mutant populations. During the sorting process the instrument was running at a speed of 22 seeds per second.

Sorting criteria were established by running a ranging sample from each mutated population (e.g., 100 Gy, 200 Gy population) and the control base variety. The ranging samples comprised approximately 1 lb (3000) seed. The predicted protein or oil content of the ranging samples were used to set sorting thresholds which were designed to segregate beans into fractions with desired compositions. The general outline for the sorting protocol is provided in FIG. 1. The sorting thresholds were based on the average protein and oil content of the population, which were determined before each sorting run, from the data collected from a ranging sample.

Figure 2:
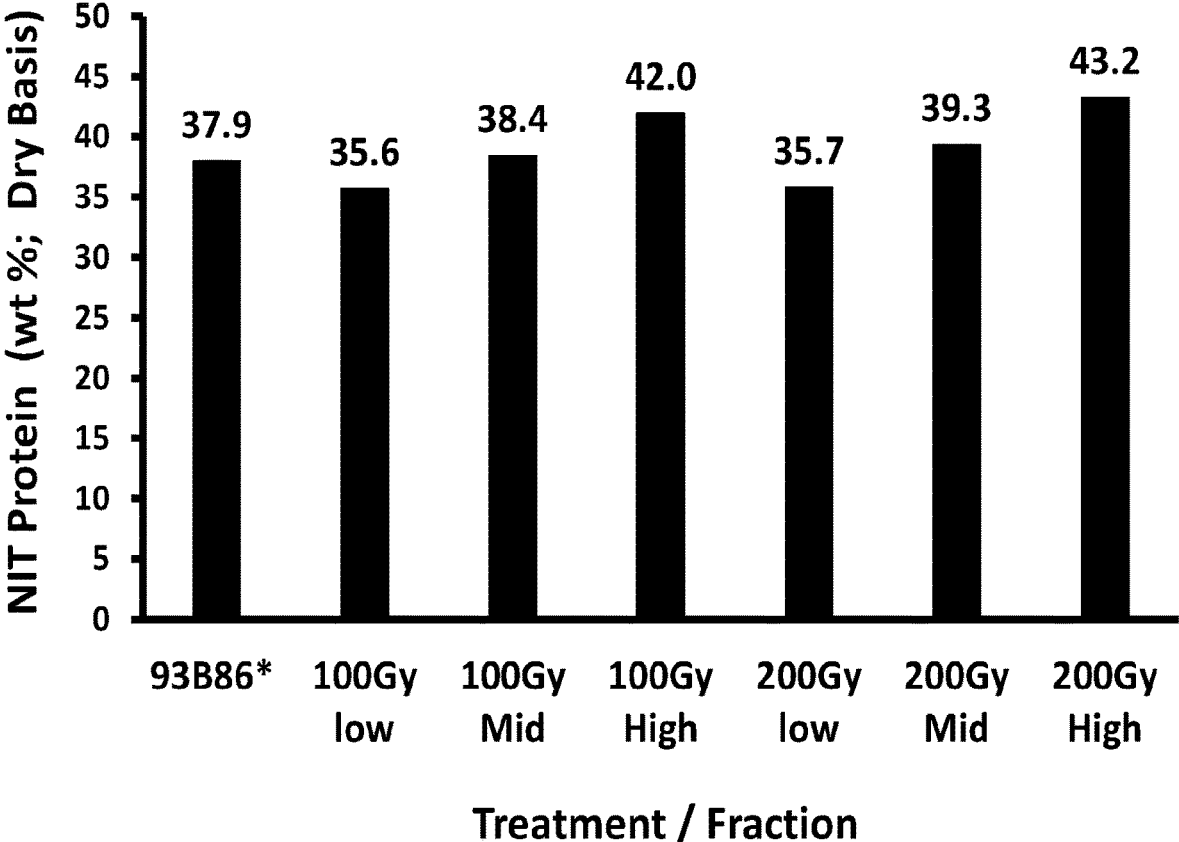
FIG. 2 is a graph of experimental results showing the protein content (wt %, dry weight basis) of the sorted fractions from the 100 and 200 Gy mutant populations as compared to a control sample.
Figure 3:
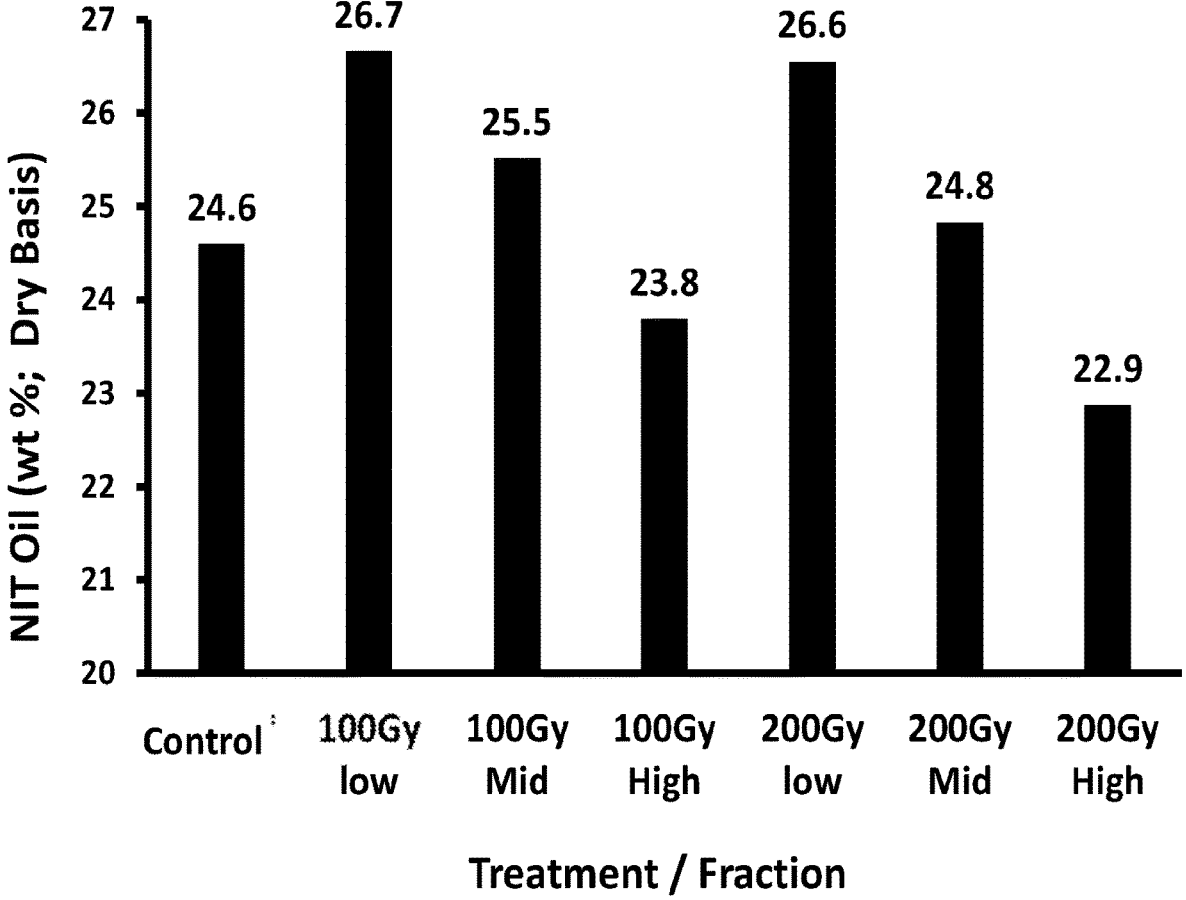
FIG. 3 is a graph of experimental results showing the oil content (wt %, dry weight basis) of the sorted fractions from the 100 and 200 Gy mutant populations as compared to a control sample.

Pooled samples of the segregated fractions were analyzed on a Foss Infratech 1241 Near Infrared grain analyzer. The protein and oil contents of the low, mid and high oil fractions (created from the initial high protein fraction (FIG. 1)) show that the average protein content of the high protein fraction was substantially higher than that of the control material (FIG. 2). The oil content of the fractions was inversely related to their protein content (FIG. 3)

Example 3

This example demonstrates a method for the generation of plants comprising seeds having increased protein and/or oil content.

Figure 4:
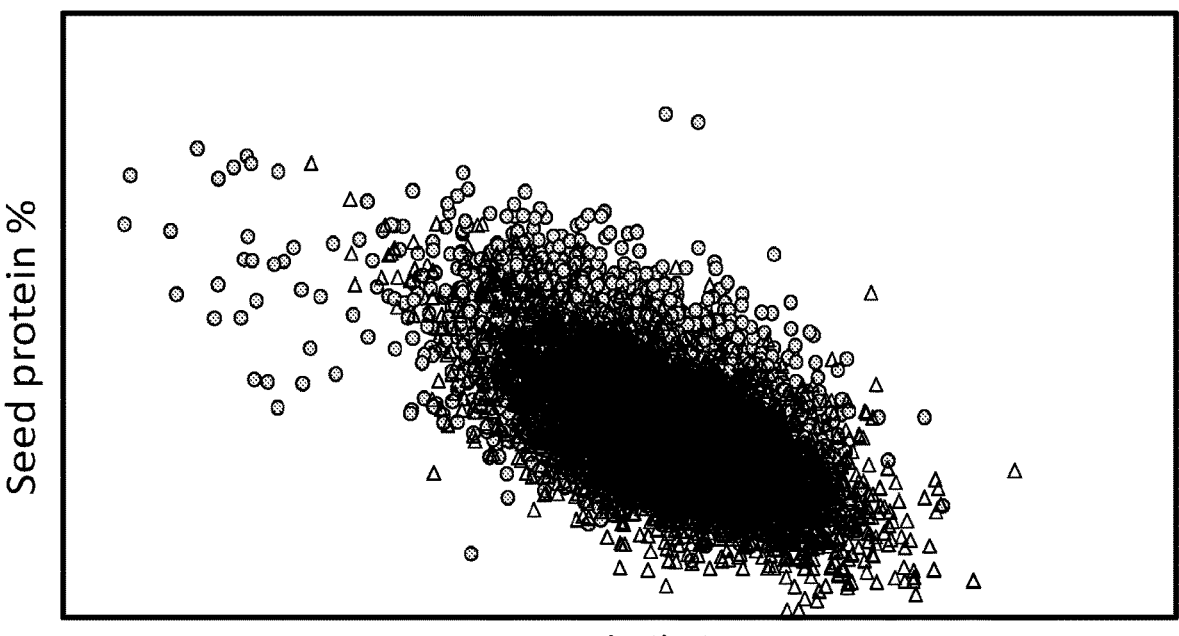
FIG. 4 is a graph showing the distribution of oil and protein content from a portion of gamma-ray M2 population compared to wild type seeds grown in the same field by a high-throughput sorter. Each dot is a single seed oil and protein content determined by high-throughput sorter.
Figure 5:
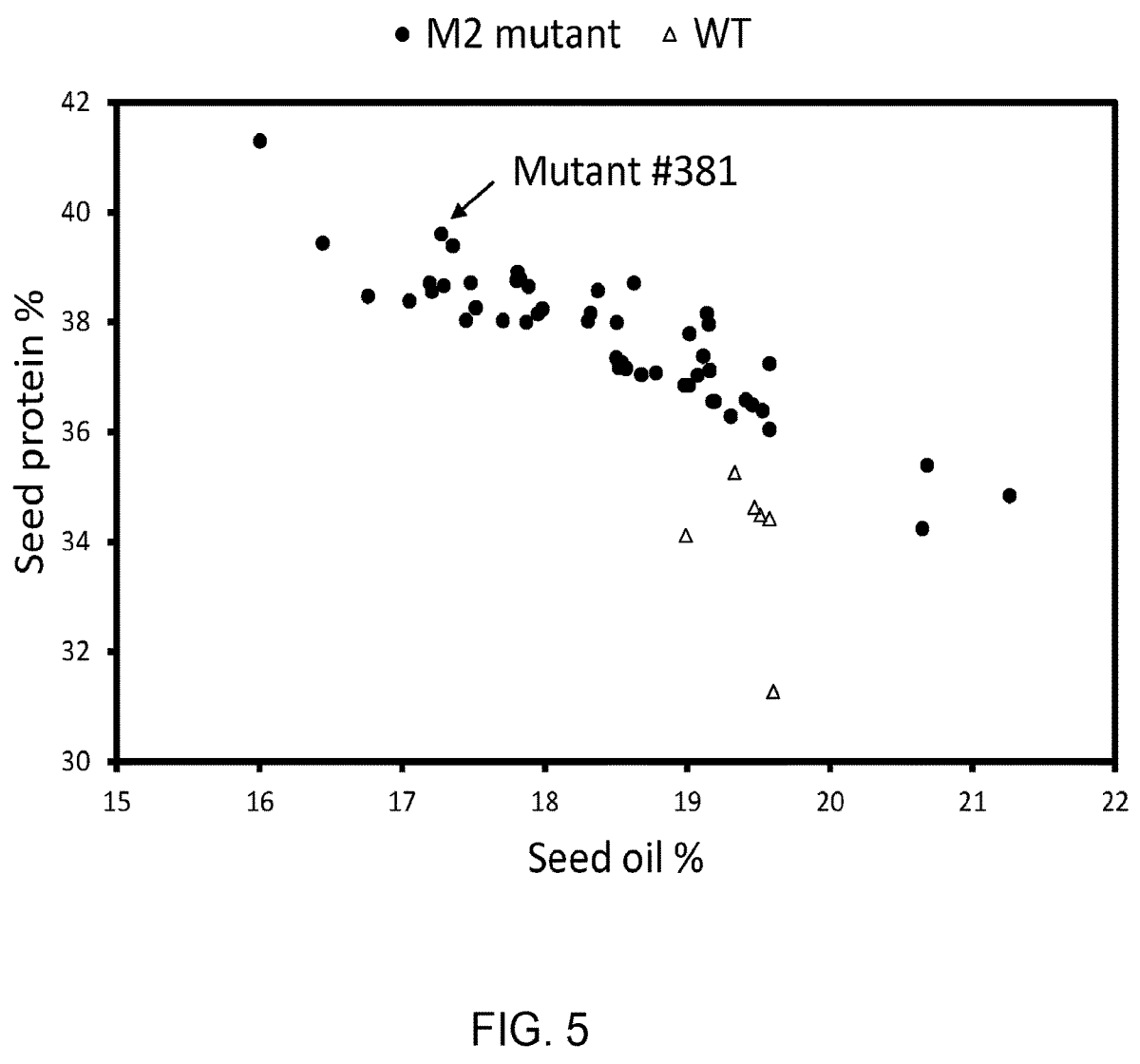
Figure 7:
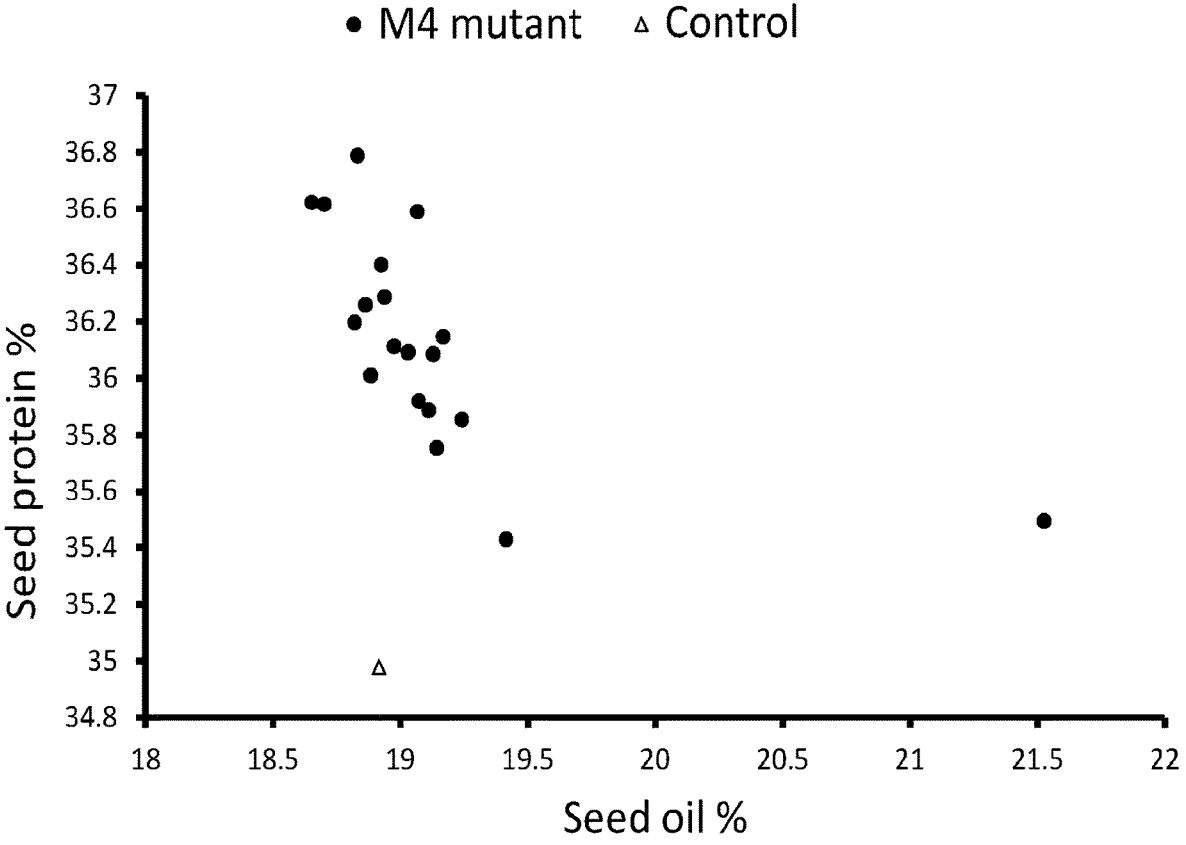
FIG. 7 is a graph of the 20 high protein and oil mutants were validated in M4 multiple row test. Each dot is the average oil and protein content at 13% moisture of multiple sublines rows by NIT.

Approximately 160 pounds of M2 seeds were harvested from the M1 plants and run through a Q-Sorter to identify high protein and oil seeds. FIG. 4 shows an example of M2 single seed oil and protein data from a portion of M2 seed population measured by the high-speed single-seed sorter. Compared to wild type seeds, the M2 seed population contains seeds with increased protein and oil which are beyond wild type seed variation. The M2 seeds were first sorted for single seeds with more than 42% seed protein content and followed by a second sorting for seeds with more than 18% oil content. After sorting for both protein and oil, approximately 5000 high protein and oil M2 seeds from 160 lb M2 seeds were identified and planted in a field at 50 seeds per short row. The plants were pulled and threshed individually. Approximately 3800 M2 plants set more than 50 seeds. Protein and oil content of all seeds from a single M2 plant was determined by an automated FT-NIR spectroscopy machine as described previously (Roesler et al., *Plant Physiol.* 2016 171:878-93). Based on seed protein and oil data, the 50 top M2 mutant plants were selected from the 3800 M2 plants and these plants were advanced for M3 validation (FIG. 5).

for each subline, and each subline was harvested by combine in bulk. Seed protein and oil content were determined by NIT as described previously (Roesler et al. *Plant Physiol.* 2016 171:878-93). Based on agronomic performance and seed composition data, 98 sublines from 20 mutants were selected for a multi-location trait efficacy validation and yield trial (FIG. 7). Leaf samples were also collected from mutant plants for whole genome sequencing. Compared to the corresponding wild type reference genome, all SNPs and deletions in the mutants were identified as candidates for co-segregation analysis.

M5 generation: Yield of high protein and oil mutants were tested in 7 locations with 2 reps per location for each subline. Each mutant has 3-12 sublines for testing. Seed protein and oil content of grain from yield plots were determined by NIT. Maturity, early vigor, and stand count were scored at field. All 20 high protein and oil mutants show high protein and oil in multiple locations with no significant inverse correlation between protein and oil. Eleven mutants showed early maturity while 8 showed a 1-3 day delay in maturity. Among the 20 mutants tested, 12 mutants were yield neutral or had a higher yield than wild type. Yield, maturity, seed oil and protein content of the 7 mutants and the wild type are shown in Table 2. Seed oil content was measured using a method equivalent to AOCS Official Method Ba 3-38, and calculated at 13% grain moisture basis. Seed protein content was measured by combustion analysis on a Flash 1112EA analyzer (Thermo) configured for N/Protein determination as described by the instrument manufacturer and calculated at 13% grain moisture basis.

The results demonstrate that the method can isolate high protein and oil mutants with no inverse protein/oil correlation and no significant impact on grain yield and agronomic traits.

TABLE 2

| | Yield, maturity, seed protein and oil content of 7 high protein and oil mutants and wild type in multi-location yield trial | | | | | | | |
|---|---|---|---|---|---|---|---|---|
| Lines | Yield (Bu/A) | Difference vs. WT | Maturity (days) | Difference vs. WT | Seed oil % | Difference vs. WT | Seed protein % | Difference vs. WT |
| WT | 58.1 | | 123 | | 18.5 | | 34.5 | |
| Mutant #1 | 57.8 | −0.3 | 122 | −1 | 18.8 | 0.3 | 36.2 | 1.7 |
| Mutant #2 | 58.2 | 0.1 | 122 | −1 | 19.2 | 0.7 | 36.3 | 1.8 |
| Mutant #3 | 56.7 | −1.4 | 121 | −2 | 19.0 | 0.5 | 36.4 | 1.9 |
| Mutant #4 | 59.2 | 1.1 | 125 | 2 | 18.7 | 0.2 | 36.7 | 2.2 |
| Mutant #5 | 58.6 | 0.5 | 125 | 2 | 18.4 | −0.1 | 37.0 | 2.5 |
| Mutant #6 | 59.5 | 1.4 | 123 | 0 | 19.4 | 0.9 | 36.3 | 1.8 |
| Mutant #7 | 59.1 | 1 | 121 | −2 | 21.4 | 2.9 | 35.7 | 1.2 |

Figure 6:
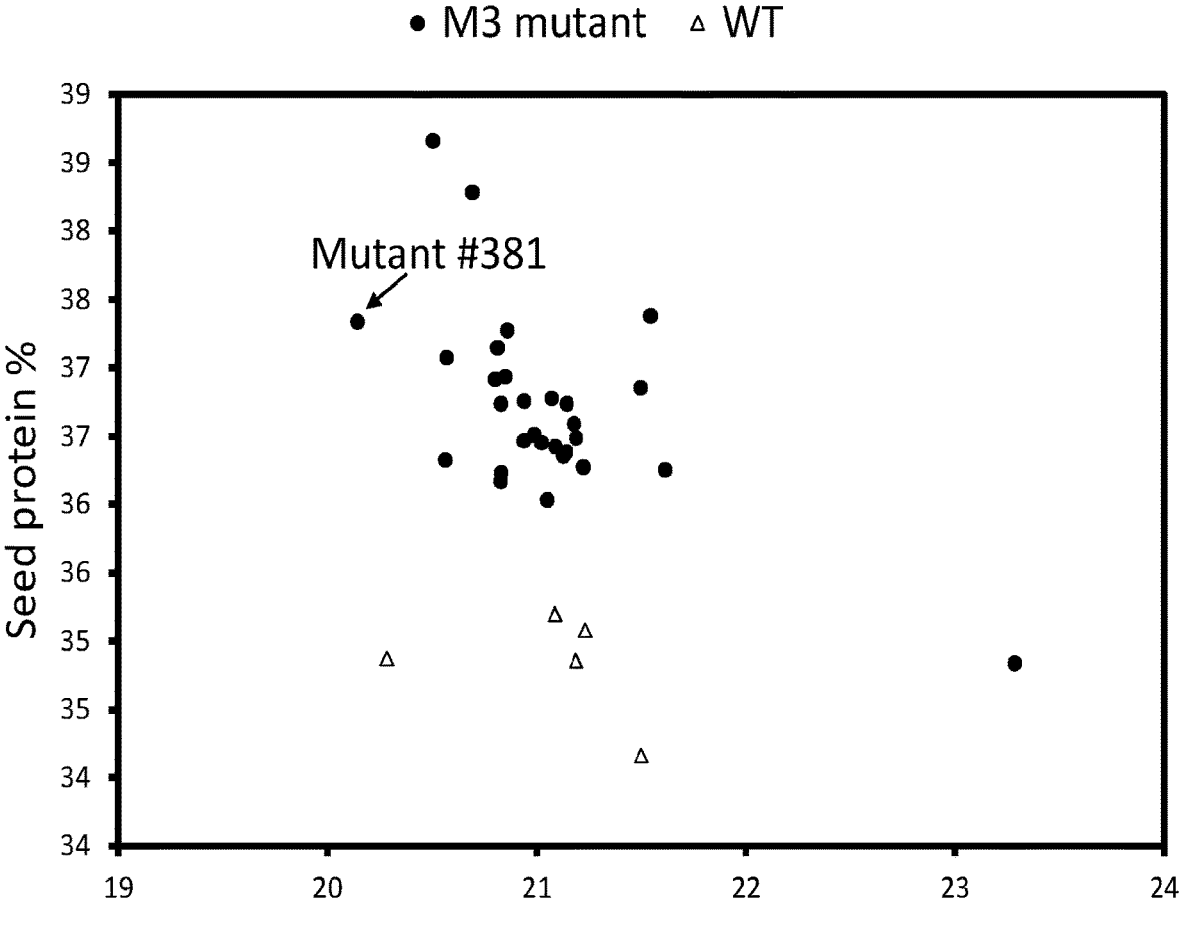
FIG. 6 is a graph of the 29 high protein and oil mutants that were validated in M3 single row test. Each dot is the average oil and protein content at 13% moisture of all plants from a single M3 mutant row by FT-NIR.

M3 generation: M3 seeds from the top 50 M2 mutant plants were grown out in a single short row in the field. Early vigor, stand count data, and maturity date were collected. At maturity, all plants in the short row were pulled and threshed individually. Seed oil and protein content from each individual M3 plant was determined by FT-NIR. Based on agronomic performance and seed composition data, 29 M3 mutants were selected to advance to M4 multiple row tests to create M4 sublines (FIG. 6).

M4 generation: About 20 plants from a single M3 mutant short row were selected based on seed protein and oil content. Each plant become a subline of the mutant and grown out at a single row. A total of approximately 620 sublines representing 31 mutants were grown out in the field. Early vigor, stand count, and maturity data were collected

Example 4

This example demonstrates the identification and prioritization of candidate mutations in the plants comprising seeds having increased protein and/or oil content.
Identification of SNPs and InDels
Raw Illumina reads produced for each sequenced soy mutant plant were processed using custom internal scripts that performs read mapping and detection of sequence variants (specifically single nucleotide polymorphisms (SNPs) or short Insertions or deletions (InDels) (~50 bp or less)). Briefly, Illumina reads were first mapped to the soybean reference genome sequence established internally. Genomic regions that contain mapped reads were parsed to identify all genomic positions wherein the base present in the reference genome sequence is different from the consensus base call, as identified by all mapped reads at that exact genomic position. This consensus base call could be a single base that is different from the reference base (in the case of a SNP), could be a short stretch of bases (in the case of a short insertion) (or) could be a gap (in the case of a short deletion). Genomic positions that are identified as containing either a SNP or InDel call, and contain at least 3 or more reads mapping at those positions, with at least 90% of the mapped bases at those positions supporting the SNP (or) InDel call, are catalogued as potential variants that exist between the mutant plant and the WT. The identified variants were further screened, based on their genomic positions, against the positions of annotated gene models within the reference genome sequence (genome annotation was established internally. Variants whose genomic positions were found to occur within the boundaries of annotated gene models were termed genic SNPs (or) InDels and were further annotated with the potential effect the variant could cause on the overlapping gene model. Each genic SNP (or) Indel was annotated as non-synonymous, if the variant causes a potential change in amino acid sequence of the annotated gene model, (or) as synonymous, if the variant does not cause a change in amino acid sequence of the annotated gene model. Variants whose genomic positions were found to occur outside the boundaries of annotated gene models were termed as intergenic SNPs (or) InDels.

Identification of Large Deletions

In addition to identifying SNPs and short InDels, the Illumina sequencing data were also analyzed using custom internal pipelines to identify large deletions (greater than 500 bp) in the genomic sequence of the soy mutant plants. The first step of this custom analysis used a sliding bin approach that binned the soybean 93B86 reference genome sequence into 500 bp bins, each bin overlapping by a window of 100 bp. Alignment files (BAMs) for each soybean mutant plant, produced during the read mapping process, were parsed using the BedTools software (v2.17.0) in order to identify a coverage value for each bin in the genome based on the fraction of the bin length that was covered by mapped reads as well as a count value for each bin in the genome based on the number of mapped reads in the bin. In the next step, genomics bins were classified as deleted bins if the coverage value calculated for the bin was less than 0.2. Deleted bins that were overlapping (or) adjacent to each other were merged into larger deleted segments and formed the set of large deletions identified in that soybean mutant plant. As with identified variants, the identified deletions were screened, based on their genomic boundaries, against the positions of annotated gene models within the reference genome sequence. Deletions were classified as genic (or) inter-genic, based on whether they overlapped the boundaries of annotated gene models. Depending on the size of the deleted segment, genic deletions may contain a portion of an annotated gene model or may overlap multiple annotated gene models entirely.

Refinement and Prioritization of Potential Causative Mutations

The above approaches identify the set of mutations (SNPs, InDels and/or large deletions) that are contained within the genome sequence of the soy mutant plant and catalog the differences between the mutant plant and the established reference genome sequence. The following steps were conducted to further refine and prioritize the set of identified mutations to a subset that is unique to each individual mutant line, that characterizes the mutant's differences from its wildtype parent and that is potentially causative for the high oil or high protein trait of interest: firstly, the mutation results identified for mutant plants (sibs) that originated from the same mutant line were combined and intersected to identify the set of the mutations that occurred in all mutant plants. This removes mutations that occurred in one or more mutant plants but not in all, thereby removing mutations that are not fixed for the trait of interest. Secondly, to address the lack of availability of sequencing data of the wildtype parent seeds used during mutagenesis, the intersected mutation result set for each mutant line was compared with intersected mutation result sets of all other mutant lines, and mutations that are not unique to any single mutant line are removed from further consideration. This process removes genetic differences identified between the wildtype parent seeds used during the mutagenesis process and the genetic material that was used to generate the reference genome sequence used for this analysis. Thirdly, unique intersected mutations that affect the amino acid sequence of annotated gene models were marked as potential causative mutations for the trait of interest and prioritized for further investigation.

Example 5

This example demonstrates the further characterization of plants comprising seeds having increased protein and/or oil content.

One of high protein mutants, named #381, shows saddle black color near hilum. Seeds collected from a single M2 plant showed 39.3% protein and 17.7% oil, compared to a wild type with 32.45 protein and 19.6% oil. All M3 plants derived from the M2 plant showed high protein phenotype relative to the control (Table 3) and all of the seed displayed a black saddle color. The whole genome of mutant #381 was sequenced. Four SNPs were identified in the mutant compared to 93B86 reference genome. No large deletion was found in mutant #381. Among 4 SNPs detected in the mutant, only one SNP with a single base deletion was found in the Argonaute 5 (AGO5) gene (glyma.11g190900) which was non-synonymous and caused an open reading frame shift in AGO5 gene (Table 4). To confirm this single base deletion in AGO 5 caused high protein and saddle color, 3 AGO 5 mutant alleles were obtained from the National Germplasm System (NGPS) (npgsweb.ars-grin.gov). All 3 AGO 5 mutants show high seed protein content and saddle seed color, indicating the mutation in AGO 5 resulted in the high protein and black saddle seed color phenotype (Table 5).

TABLE 3

Seed protein and oil content of mutant #381 M3 plants

| M3 plant | Seed Oil % | Seed Protein % |
|---|---|---|
| WT | 21.1 | 34.4 |
| Mutant plant 1 | 19.9 | 36.7 |
| Mutant plant 2 | 20.0 | 37.4 |
| Mutant plant 3 | 20.9 | 37.7 |
| Mutant plant 4 | 19.4 | 39.1 |
| Mutant plant 5 | 20.4 | 36.8 |
| Mutant plant 6 | 20.3 | 37.5 |
| Mutant plant 7 | 19.8 | 38.4 |
| Mutant plant 8 | 21.0 | 36.0 |
| Mutant plant 9 | 21.6 | 35.1 |
| Mutant plant 10 | 20.2 | 37.0 |
| Mutant plant 11 | 19.2 | 37.9 |
| Mutant plant 12 | 20.3 | 37.0 |
| Mutant plant 13 | 20.1 | 37.9 |
| Mutant plant 14 | 20.3 | 37.0 |

TABLE 3-continued

Seed protein and oil content of mutant #381 M3 plants

| M3 plant | Seed Oil % | Seed Protein % |
|---|---|---|
| Mutant plant 15 | 20.1 | 37.7 |
| Mutant plant 16 | 20.6 | 37.7 |
| Mutant plant 17 | 19.6 | 37.9 |
| Mutant plant 18 | 20.9 | 36.9 |
| Mutant plant 19 | 20.3 | 37.0 |
| Mutant plant 20 | 19.5 | 38.0 |
| Mutant plant 21 | 20.3 | 36.6 |
| Mutant plant 22 | 20.1 | 36.8 |

TABLE 4

Mutations in high protein mutant #381

| Gene | Annotation | Function |
|---|---|---|
| glyma.07g206500 | intronic | SAC9 protein-like protein |
| glyma.09g223700 | UTR | Putative Glycerol-3-phosphate transporter |
| glyma.11g190900 | nonsynonymous | Protein argonaute 5 |
| glyma.17g003200 | intronic | Glutathione S-transferase 2 isoform 2 |

TABLE 5

Seed protein content and saddle color of 3 AGO 5 mutant alleles

| Soybean line | Name | Mutation in Ago5 | Seed protein content % | Seed color |
|---|---|---|---|---|
| PI548362 | Lincoln parent | wild type | 42.1 | yellow |
| PI634896 | Saddle mutant from Lincoln 1954 | a STOP codon at Exon 13 | 46.3 | black saddle |
| PI634895 | Saddle mutant from Lincoln 1945 | 4 aa deletion at Exon 10 | 44.3 | black saddle |
| PI548527 | Calland parent | wild type | 43.3 | yellow |
| PI634873 | Saddle mutant from Calland 1970 | missing first ATG | 47.0 | black saddle |

All publications and patent applications in this specification are indicative of the content of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

We claim:

1. A method for producing plants having seeds with increased protein or oil from a mutagenized population of seeds, the method comprising:

(a) providing a mutagenized population of seeds, the mutagenized population of seeds having a genetic background modified by mutations introduced by random mutagenesis;

(b) performing a high-throughput near infrared single-seed, non-destructive measurement of the protein or oil content of a sample of seeds comprising a subset of the mutagenized population of seeds, a corresponding control, or a combination thereof;

(c) setting a threshold protein or oil value based upon the measurement of protein or oil content respectively of the sample of seeds, wherein the threshold protein or oil value is set above the average of the protein or oil content of the sample of seeds;

(d) separating seeds that exceed the threshold protein or oil value from the mutagenized population of seeds;

(e) generating plants from the separated seeds that exceed the threshold protein or oil value, wherein the plants comprise an introduced mutation resulting in increased protein or oil;

(f) collecting seeds from individual plants produced in (e), wherein the individual plants are optionally chosen based on one or more agronomic or seed composition characteristics;

(g) determining the average protein and/or oil content of the seeds collected from an individual plant in (f) using a second non-destructive analysis;

(h) identifying plants that produce seeds having an average protein and/or oil content that achieves a second threshold protein value and/or a second threshold oil value, wherein the second threshold protein value is a plant average seed protein content of at least 34% by weight at 13% moisture, the second threshold oil value is a plant average seed oil content of at least 16% by weight at 13% moisture, or the second threshold oil value is both a plant average seed protein content of at least 34% by weight at 13% moisture and a plant average seed oil content of at least 16% by weight at 13% moisture;

(i) selecting the seeds from the plants of (h) that achieve the second threshold protein value and/or the second threshold oil value; and (j) generating plants from the seed selected in (i).

2. A method for producing plants having seeds with increased oil and protein from a mutagenized population of seeds, the method comprising:

(a) providing a mutagenized population of seeds, the mutagenized population of seeds having a genetic background modified by mutations introduced by random mutagenesis;

(b) performing a high-throughput near infrared single-seed, non-destructive measurement of the protein and oil content of a sample of seeds comprising a subset of the mutagenized population of seeds, a corresponding control, or a combination thereof;

(c) setting a threshold protein and oil value based upon the measurement of protein and oil content of the sample of seeds, wherein the threshold value is set above the average of the protein and oil content of the sample of seeds;

(d) separating seeds that exceed the threshold oil and protein value from the mutagenized population of seeds; and (e) generating plants from the separated seeds that exceed the threshold protein and oil value, wherein the plants comprise an introduced mutation resulting in increased protein and oil;

(f) collecting seeds from individual plants produced in (e), wherein the individual plants are optionally chosen based on one or more agronomic or seed composition characteristics;

(g) determining the average protein and/or oil content of the seeds collected from an individual plant in (f) using a second non-destructive analysis;

(h) identifying plants that produce seeds having an average protein and oil content that achieves a second threshold protein value and a second threshold oil value, wherein the second threshold protein value is a plant average seed protein content of at least 34% by weight at 13% moisture and the second threshold oil value is a plant average seed oil content of at least 16% by weight at 13% moisture;

(i) selecting the seeds from the plants of (h) that achieve the second threshold protein value and the second threshold oil value; and (j) generating plants from the seed selected in (i).

3. The method of claim 1, further comprising prior to step (e)

(i) performing a high-throughput near infrared single-seed, non-destructive measurement of the protein content of the seeds from step (d) when the oil content is measured in step (b) or the oil content of the seeds from step (d) when the protein content is measured in step (b);

(ii) setting a threshold protein value based upon the measurement of protein content of the seeds in step (i) or a threshold oil value based upon the measurement of oil content of the seeds in step (i), wherein the threshold protein or oil value is set above the average of the protein or oil content respectively of the of seeds of step (i); and (iii) separating seeds that exceed the threshold values set in step (ii) from the seeds measured in step (i).

4. The method of claim 1, wherein the genetic background of the mutagenized population of seeds is at least 90% homozygous.

5. The method of claim 1, wherein the mutagenized population of seeds comprising one or more introduced mutations comprises between 2000 to 10 million seeds and the sample of seeds of comprises between 1000 to 50,000 seeds.

6. The method of claim 1, wherein the method further comprises repeating steps (b) to (e) at least once.

7. The method of claim 1, wherein the high-throughput single seed non-destructive measurement comprises the use of single seed near infrared spectroscopy (SS-NIR).

8. The method of claim 1, wherein the accuracy of the single seed non-destructive protein measurement or single seed non-destructive oil measurement is within 15% of the protein amount or oil amount measured using a standard wet chemistry reference analytical method of the seed.

9. The method of claim 1, wherein the threshold protein value is a protein value that is at least 1.5 percentage points higher than the average protein value of the sample of seeds or the threshold oil value is an oil value that is at least 0.5 percentage points higher than the average oil value of the sample of seeds.

10. The method of claim 1, wherein the threshold protein value or threshold oil value is set to separate at least 0.5% and less than 20% of the seeds from the sample of seeds in step (d).

11. The method of claim 1, wherein the second non-destructive analysis comprises a near infrared spectroscopy (NIRS) method selected from the group consisting of near infrared reflectance (NIR), near infrared transmittance (NIT), single seed NIR (SS-NIR), bulk NIT, or Fourier transform NIR (FT-NIR).

12. The method of claim 1, wherein the individual plants in step (f) are chosen based on at least one characteristic selected from the group consisting of disease resistance, insect resistance, herbicide resistance, yield, early vigor, stand count, grain quality, amino acid content, sucrosyl-oligosaccharide content, plant height, nitrogen use efficiency, drought resistance, standability, abiotic stress resistance, and relative maturity.

13. The method of claim 1, wherein the method further comprises determining the yield of the plants generated in (j) and selecting plants that have a yield higher than or within 3% as compared to a corresponding control plant.

14. The method of claim 1, wherein the method further comprises:

(k) collecting seeds from individual plants generated in (j), wherein the individual plants are optionally chosen based on one or more agronomic or seed composition characteristics;

(l) determining the average protein and/or oil content of the seeds collected from an individual plant of (k) using a third non-destructive analysis;

(m) identifying plants that produce seeds having a seed protein and/or oil content that achieves a third threshold protein value and/or a third threshold oil value;

(n) selecting the seeds from the individual plants in (m) that achieve the third threshold protein value and/or the third threshold oil value; and (o) generating plants from the seed selected in (n).

15. The method of claim 14, wherein the method further comprises:

(p) collecting seeds from individual plants generated in (o), wherein the individual plants are optionally chosen based on one or more agronomic or seed composition characteristics;

(q) determining the average protein and/or oil content of the seeds collected from an individual plant of (p) using a fourth non-destructive analysis;

(r) identifying plants that produce seeds having a protein content and/or oil content that achieves a fourth average threshold protein value and/or a fourth average threshold oil value;

(s) selecting the seeds from the individual plants identified in (r) that achieve a fourth average threshold protein value and/or a fourth average threshold oil value; and (t) generating plants from the seed selected in(s).

16. The method of claim 1, further comprising introducing mutations into a population of seeds to produce the mutagenized population of seeds prior to step (a) by:

(i) treating a collection of seeds with a mutagen to produce a mutant population of seeds;

(ii) growing plants comprising one or more introduced mutations from the mutant seed population; and (iii) collecting the mutagenized population of seeds from the plants grown in step (ii).

17. The method of claim 16, wherein the mutagen is gamma ray, neutrons, or ethyl methanesulfonate (EMS).

18. The method of claim 1, wherein the plant is selected from the group consisting of cotton, soybean, *Brassica*, and maize.

19. The method of claim 2, wherein the individual plants in step (f) are chosen based on at least one characteristic selected from the group consisting of disease resistance, insect resistance, herbicide resistance, yield, early vigor, stand count, grain quality, amino acid content, sucrosyl-oligosaccharide content, plant height, nitrogen use efficiency, drought resistance, standability, abiotic stress resistance, and relative maturity.

20. The method of claim 2, wherein the method further comprises determining the yield of the plants generated in (j) and selecting plants that have a yield higher than or within 3% as compared to a corresponding control plant.

* * * * *